(12) United States Patent
Green et al.

(10) Patent No.: US 7,332,174 B2
(45) Date of Patent: Feb. 19, 2008

(54) MUTANT FORMS OF CHOLERA HOLOTOXIN AS AN ADJUVANT

(75) Inventors: Bruce A. Green, New City, NY (US); Randall K. Holmes, Golden, CO (US); Michael G. Jobling, Aurora, CO (US); Duzhang Zhu, Pomona, NY (US)

(73) Assignees: Wyeth Holdings Corporation, Madison, NJ (US); The United States of America as represented by the Uniformed Services University of Health Sciences, Washington, DC (US)

( * ) Notice: Subject to any disclaimer, the term of this patent is extended or adjusted under 35 U.S.C. 154(b) by 507 days.

(21) Appl. No.: 10/478,308

(22) PCT Filed: Jun. 5, 2002

(86) PCT No.: PCT/US02/21008

§ 371 (c)(1),
(2), (4) Date: Dec. 4, 2003

(87) PCT Pub. No.: WO02/098369

PCT Pub. Date: Dec. 12, 2002

(65) Prior Publication Data

US 2004/0176571 A1    Sep. 9, 2004

Related U.S. Application Data

(60) Provisional application No. 60/296,531, filed on Jun. 7, 2001.

(51) Int. Cl.
*A61K 39/106* (2006.01)
*C07K 1/00* (2006.01)

(52) U.S. Cl. .............. 424/261.1; 530/350; 424/203.1; 424/201.1

(58) Field of Classification Search ............... None
See application file for complete search history.

(56) References Cited

U.S. PATENT DOCUMENTS

| | | | |
|---|---|---|---|
| 4,666,829 A | | 5/1987 | Glenner et al. |
| 4,883,761 A | * | 11/1989 | Keith et al. ............ 435/252.33 |
| 5,601,831 A | | 2/1997 | Green et al. |
| 5,643,747 A | * | 7/1997 | Baker et al. ................ 435/69.1 |
| 5,786,189 A | * | 7/1998 | Locht et al. ............. 424/200.1 |
| 5,925,546 A | | 7/1999 | Pizza et al. |
| 6,040,427 A | * | 3/2000 | Locht et al. ................ 530/350 |
| 6,685,949 B1 | | 2/2004 | Gu et al. |
| 7,105,161 B1 | * | 9/2006 | Gajewczyk et al. ..... 424/184.1 |
| 2003/0176653 A1 | | 9/2003 | Mason et al. |
| 2004/0181036 A1 | | 9/2004 | Green et al. |
| 2005/0175631 A1 | | 8/2005 | Vajdy et al. |
| 2006/0057155 A1 | * | 3/2006 | Masignani et al. ...... 424/190.1 |
| 2006/0069052 A1 | * | 3/2006 | Hone ............................ 514/44 |
| 2006/0177469 A1 | | 8/2006 | Rappuoli |
| 2006/0251675 A1 | | 11/2006 | Hagen |

FOREIGN PATENT DOCUMENTS

| | | | |
|---|---|---|---|
| WO | 95/17211 | * | 6/1995 |
| WO | 98/42375 | * | 10/1998 |
| WO | WO 99/27944 | | 6/1999 |
| WO | WO 02/098369 A2 | | 12/2002 |

OTHER PUBLICATIONS

Glineur et al, Infection and Immunity, Oct. 1994, vol. 62(10), pp. 4176-4183, Importance of ADP-Ribosylation in the morphological changes of PC12 cells induced by Cholera toxin.*

Cortina, Galen et al, The Journal of Biological Chemistry, vol. 264(29), Oct. 15, 1989, pp. 17322-17328, Role of Tryptophan 26 in the NAD Glycohydrolase reaction of the S-1 sucunit of pertussis toxin.*

Barbieri, JT et al, Infection and Immunity, vol. 56(8), pp. 1934-1942, Aug. 1988, ADP-Ribosyltransferase mutations in the catalytic S-1 subunit of Pertussis toxin.*

Jobling, Michael G et al, Journal of Bacteriology, Jul. 2001, vol. 183(13), pp. 4024-4032, Biological and Biochemical Characterization of Variant A subunits of cholera toxin constructed by site-directed mutagenesis.*

Locht, Camille et al, PNAS (USA), vol. 86, pp. 3075-3079, May 1989, Identification of amino acid residues essential for the enzymatic activities of pertussis toxin.*

Holmes, Randall K et al, Chapter 10, pp. 225-244, cholera toxin and related enterotoxins of Gram-Negative bacteria, 1995.*

Feil et al., "Protein engineering studies of A-chain loop 47-56 of *Escherichia coli* heat-labile enterotoxin point to a prominent role of this loop for cytotoxicity", Mol Microbiol. May 1996, 20(4):823-32.

Jobling et al., "Fusion proteins containing the A2 domain of cholera toxin assemble with B polypeptides of cholera toxin to form immunoreactive and functional holotoxin-like chimeras", Infect Immun. Nov. 1992, 60(11):4915-24.

Lobet et al., "Effect of site-directed mutagenic alterations on ADP-ribosyltransferase activity of the A subunit of *Escherichia coli* heat-labile enterotoxin", Infection and Immunity Sep. 1991 59(9):2870-2879.

Orkin et al., "Report and Recommendations of the Panel to Assess the NIH Investment in Research on Gene Therapy", Dec. 7, 1995.

Shi et al., GENBANK Accession No. AAC34728, 1993.

Tebbey et al., "Effective mucosal immunization against respiratory syncytial virus using purified F protein and a genetically detoxified cholera holotoxin, CT-E29H", Vaccine, Jun. 1, 2000;18(24):2723-34.

(Continued)

*Primary Examiner*—Mark Navarro
*Assistant Examiner*—Ginny Allen Portner
(74) *Attorney, Agent, or Firm*—Howson & Howson LLP; J. Darrell Fontenot

(57) ABSTRACT

Mutant cholera holotoxins having single or double amino acid substitutions or insertions have reduced toxicity compared to the wild-type cholera holotoxin. The mutant cholera holotoxins are useful as adjuvants in antigenic compositions to enhance the immune response in a vertebrate host to a selected antigen from a pathogenic bacterium, virus, fungus, or parasite, a cancer cell, a tumor cell, an allergen, or a self-molecule.

21 Claims, No Drawings

OTHER PUBLICATIONS

Zhang et al., "The three-dimensional crystal structure of cholera toxin", J Mol Biol. Aug. 25, 1995, 251(4):563-73.
International Patent Publication No. WO 98/42375A, published Oct. 1, 1998.
International Patent Publication No. WO 98/45324A, published Oct. 15, 1998.
Communication- Supplementary European Search Report in European Application No. EP 02752145, mailed Apr. 21, 2006.
Sanchez, et al., Detoxification of Cholera Toxin without Removal of Its Immunoadjuvanticity by the Addition of (STa-related) Peptides to the Catalytic Subunit, J. Biol. Chem., Sep. 6, 2002, pp. 33369-33377, vol. 277, No. 36.

* cited by examiner

MUTANT FORMS OF CHOLERA HOLOTOXIN AS AN ADJUVANT

CROSS-REFERENCE TO OTHER APPLICATIONS

This application is a national stage of International Patent Application No. PCT/US02/21008, filed Jun. 5, 2002, which claims the benefit of the priority under 35 USC 119(e) of U.S. Provisional Patent Application No. 60/296,531, filed Jun. 7, 2001.

BACKGROUND OF THE INVENTION

The body's immune system activates a variety of mechanisms for attacking pathogens (Janeway, Jr, C A. and Travers P., eds., in *Immunobiology*, "The Immune System in Health and Disease," Second Edition, Current Biology Ltd., London, Great Britain (1996)). However, not all of these mechanisms are necessarily activated after immunization. Protective immunity induced by immunization is dependent on the capacity of an immunogenic composition to, elicit the appropriate immune response to resist or eliminate the pathogen. Depending on the pathogen, this may require a cell-mediated and/or humoral immune response.

Many antigens are poorly immunogenic or non-immunogenic when administered by themselves. Strong adaptive immune responses to antigens almost always require that the antigens be administered together with an adjuvant, a substance that enhances the immune response (Audbert, F. M. and Lise, L. D. 1993 *Immunology Today*, 14: 281-284).

The need for effective immunization procedures is particularly acute with respect to infectious organisms that cause acute infections at, or gain entrance to the body through, the gastrointestinal, pulmonary, nasopharyngeal or genitourinary surfaces. These areas are bathed in mucus, which contains immunoglobulins consisting largely of secretoty immunoglobulin IgA (Hanson, L. A., 1961 *Intl. Arch. Allergy. Appl. Immunol.*, 18, 241-267; Tomasi, T. B., and Zigelbaum, S., 1963 *J. Clin. Invest.*, 42, 1552-1560; and Tomasi, T. B., et al., 1965 *J. Exptl. Med.*, 121, 101-124). This immunoglobulin is derived from large numbers of IgA-producing plasma cells, which infiltrate the larnina propria regions underlying the mucosal membranes (Brandtzaeg, P., and Baklein, K, *Scand.* 1976 *J. Gastroenterol.*, 11 (Suppl. 36), 1-45; and Brandtzaeg, P., 1984 "Immune Functions of Human Nasal Mucosa and Tonsils in Health and Disease", page 28 et seq. in *Immunology of the Lung and Upper Respiratory Tract*, Bienenstock, J., ed., McGraw-Hill, New York, N.Y.). The secretory immunoglobulin IgA is specifically transported to the luminal surface through the action of the secretory component (Solari, R, and Kraehenbuhl, J-P, 1985 *Immunol. Today*, 6, 17-20).

Parenteral immunization regimens are usually ineffective in inducing secretory IgA responses. Secretory immunity is most often achieved through the direct immunization of mucosally associated lymphoid tissues. Following their induction at one mucosal site, the precursors of IgA-producing plasma cells extravasate and disseminate to diverse mucosal tissues where final differentiation to high-rate IgA synthesis occurs (Crabbe, P. A, et al., 1969 *J. Exptl. Med.*, 130, 723-744; Bazin, H., et al., 1970 *J. Immunol.*, 105, 1049-1051; Craig, S. W., and Cebra, J. J., 1971 *J. Exptl. Med.*, 134, 188-200). Extensive studies have demonstrated the feasibility of mucosal immunization to induce this common mucosal immune system (Mestecky, J., et al., 1978 *J. Clin. Invest.*, 61, 731-737). With rare exceptions the large doses of antigen required to achieve effective immunization have made this approach impractical for purified antigens.

Among the strategies investigated to overcome this problem is the use of mucosal adjuvants. A number of adjuvants that enhance the immune response of antigens are known in the prior art (Elson, C. O., and Ealding, W., 1984 *J. Immunol.*, 132, 2736-2741). These adjuvants, when mixed with an antigen, render the antigen particulate, helping retain the antigen in the body for longer periods of time, thereby promoting increased macrophage uptake and enhancing immune response. However, untoward reactions elicited by many adjuvants or their ineffectiveness in inducing mucosal immunity have necessitated the development of better adjuvants for delivery of immunogenic compositions. Unfortunately, adjuvant development to date has been largely an empirical exercise (Janeway, Jr., et al, cited above at pages 12-25 to 12-35). Thus, a rational and a more direct approach is needed to develop effective adjuvants for delivery of antigenic compositions.

It has been reported that the toxin secreted by the Gram-negative bacterium *Vibrio cholerae* (*V. cholerae*), the causative agent of the gastrointestinal disease cholera, is extremely potent as an adjuvant. Cholera toxin (CT) has been reported as a 382 amino acid sequence (SEQ ID NO: 1) (Mekalanos, J. J., et al, 1983 *Nature*, 306, 551-557), which has an 18 amino acid signal (amino acids 1 to 18 of SEQ ID NO: 1). The cholera toxin holotoxin molecule is a hexaheteromeric complex that consists of a single peptide subunit designated CT-A (SEQ ID NO: 2 or amino acids 19 to 258 of SEQ ID NO: 1), which is responsible for the enzymatic activity of the toxin, and five identical peptide subunits, each designated CT-B (each having a 21 amino acid signal (amino acids 259 to 279 of SEQ ID NO:1), followed by the CT-B peptide subunit (amino acids 280 to 382 of SEQ ID NO: 1)), which are involved in the binding of the toxin to the intestinal epithelial cells as well as other cells which contain ganglioside $GM_1$ on their surface (Gill, D. M., 1976 *Biochem.*, 15, 1242-1248; Cuatrecasas, P., 1973 *Biochem.*, 12, 3558-3566). CT produced by *V. cholerae* has the CT-A subunit proteolytically cleaved within the single disulfide-linked loop between the cysteines at amino acid positions 187 and 199 of the mature CT-A (SEQ ID NO: 2). This cleavage produces an enzymatically active A1 polypeptide (Kassis, S., et al., 1982 *J. Biol. Chem.*, 257, 12148-12152) and a smaller polypeptide A2, which links fragment A1 to the CT-B pentamer (Mekalanos, J. J., et al., 1979 *J. Biol. Chem.*, 254, 5855-5861). Toxicity results when the enzymatically active fragment CT-A1, upon entry into enterocytes, ADP-ribosylates a regulatory G-protein (Gsα). This leads to constitutive activation of adenylate cyclase, increased intracellular concentration of cAMP, and secretion of fluid and electrolytes into the lumen of the small intestine (Gill, D. M., and Meren, R, 1978 *Proc. Natl. Acad. Sci., USA*, 75, 3050-3054), thereby causing toxicity. In vitro, ADP-ribosyl transferase activity of CT is stimulated by the presence of accessory proteins called ARFs, small GTP-binding proteins known to be involved in vesicle trafficking within the eukaryotic cell (Welsh, C. F., et al., "ADP-Ribosylation Factors: A Family of Guanine Nucleotide-Binding Proteins that Activate Cholera Toxin and Regulate Vesicular Transport", pages 257-280 in *Handbook of Natural Toxins: Bacterial Toxins and Virulence Factors in Disease Vol.* 8 (Moss, J., et al., eds., Marcel Dekker, Inc., New York, N.Y. 1995).

Co-administration of CT with an unrelated antigen has been reported to result in the induction of concurrent circulating and mucosal antibody responses to that antigen (Mekalanos, J. J., et al., 1983 *Nature,* 306, 551-557). To minimize the occurrence of undesirable symptoms such as diarrhea caused by wild-type CT in humans, it would be preferable to use as an adjuvant a form of the CT holotoxin that has substantially reduced toxicity. Mutants of CT have been suggested as a means for achieving a more useful adjuvant. One way to rationally design mutant cholera toxin holotoxins (designated CT-CRMs) with substantially reduced toxicity is to identify and alter amino acid residues in the toxin molecule that are completely conserved in the family of cholera (CT) and related heat-labile enterotoxins (LT-I, LT-IIa and LT-IIb) of *E. coli*. Another rational way to generate mutant CT-CRMs with substantially reduced toxicity is to alter amino acid residues in the holotoxin molecule that have been identified as being important for NAD-binding based on the structural alignment of the CT backbone with the backbone of related toxins possessing ADP-ribosyl transferase enzyme activity such as diphtheria toxin (DT) and pertussis toxin (PT) (Holmes, R K, "Heat-labile enterotoxins (*Escherichia coli*)" in *Guidebook to Protein Toxins and their Use in Cell Biology*, Montecucco, C. and Rappnoli, R., Eds., Oxford Univ. Press, Oxford, England (1997); and Holmes, R. K et al, "Cholera toxins and related enterotoxins of Gram-negative bacteria", pp. 225-256 in *Handbook of Natural Toxins: Bacterial Toxins and Virulence Factors in Disease*, vol. 8, Moss. J., et al, Eds., Marcel Dekker, Inc., New York, N.Y. 1995).

Recently, one such rationally-designed, genetically-detoxified mutant of CT was disclosed wherein a single nonconservative amino acid substitution (glutamic acid to histidine) was introduced by altering the amino acid at position 29 in the mature A subunit (designated CT-CRM$_{E29H}$). The resulting mutant cholera holotoxin demonstrated substantially reduced enzymatic toxicity, but with superior adjuvanting and immunogenic properties (International Patent Publication No. WO 00/18434, incorporated in its entirety by reference).

Thus, there is a need to identify and/or rationally design additional mutant forms of the CT holotoxin that have substantially reduced toxicity, yet possess the same or enhanced adjuvanting properties as the wild-type CT holotoxin.

SUMMARY OF THE INVENTION

In one aspect, this invention provides novel mutant, immunogenic forms of cholera holotoxin (designated CT-CRMs) having significantly reduced toxicity compared to wild-type cholera holotoxin (CT), but which retain the ability to function as powerful stimulators of the immune system. Specifically, the invention pertains to five mutant cholera holotoxins (CT-CRMs), desirably generated by site-directed mutagenesis and having substantially reduced toxicity compared to wild-type CT, but with no loss in adjuvanting properties.

In one embodiment, a novel CT-CRM of this invention comprises the amino acid sequence of CT subunit A or a fragment thereof, wherein the amino acid residue in the amino acid position 25 of the A subunit is substituted with another amino acid, which substitution results in a substantial reduction in toxicity. In a preferred embodiment of the invention, the amino acid arginine at amino acid position 25 of the A subunit is substituted with a tryptophan or a glycine. For determination of the amino acid position, the sequence of CT-A is exemplified in SEQ ID NO: 2. However, other variants and fragments of CT-A may also be employed.

In another embodiment, a novel immunogenic mutant CT-CRM of this invention comprises the amino acid sequence of CT subunit A or a fragment thereof, wherein there is an insertion of a single amino acid residue in the amino acid position 49 of the A subunit, which insertion results in a substantial reduction in toxicity. In this aspect and throughout this application, whenever it is stated that "there is an insertion of a single (or multiple) amino acid residue(s) in the A subunit", this means that the wild-type residue(s) in amino acid position(s) [insert amino acid number(s)] is (are) shifted downstream. In a preferred embodiment of the invention, the amino acid residue histidine is inserted in the amino acid position 49 of the A subunit, thereby shifting the amino acid residues originally located at positions 49, 50, etc., to positions 50, 51, etc.

In a third embodiment, a novel immunogenic, mutant CT-CRM of this invention has substantially reduced CT toxicity and comprises the amino acid sequence of subunit A of CT or a fragment thereof, wherein there is an insertion of two amino acid residues in the amino acid positions 35 and 36 in the A subunit, which insertion results in a substantial reduction in toxicity. In a preferred embodiment of this aspect of the invention, the amino acid residues glycine and proline are inserted at the amino acid positions 35 and 36 in the A subunit, thereby shifting the original amino acid residues at positions 35 and 36 to positions 37 and 38, etc.

In yet another embodiment, a novel immunogenic, mutant CT-CRM of this invention has substantially reduced CT toxicity and comprises the amino acid sequence of subunit A of CT or a fragment thereof, wherein there is an amino acid substitution in the amino acid residue 30 of the A subunit and an insertion of two amino acid residues in the amino acid positions 31 and 32 in the A subunit, which substitution and insertion results in a substantial reduction in toxicity. In a preferred embodiment of this aspect of the invention, the amino acid tryptophan is substituted for tyrosine at amino acid position 30 of the A subunit, and the amino acid residues alanine and histidine are inserted in the amino acid positions 31 and 32, respectively, in the A subunit, thereby shifting the original amino acid residues at positions 31 and 32 to positions 33 and 34, etc.

In another aspect, the invention provides a method for producing the novel CT-CRMs described above by employing site-directed mutagenesis of the DNA encoding the A subunit in the wild-type CT using conventional techniques, such that the mutagenized CT now has substantially reduced toxicity without compromising the toxin's ability to stimulate an immune response.

In yet another aspect of the invention, there is provided an immunogenic composition comprising a selected antigen, a mutant CT-CRM as described above as an adjuvant to enhance the immune response in a vertebrate host to the antigen, and a pharmaceutically acceptable diluent, excipient or carrier. Preferably, the CT-CRM is useful for the generation or enhancement of systemic and/or mucosal antigenic immune responses in a vertebrate host to the selected antigen. The selected antigen may be a polypeptide, peptide or fragment derived from a pathogenic virus, bacterium, fungus or parasite. The selected antigen may be a polypeptide, peptide or fragment derived from a cancer cell or tumor cell. The selected antigen may be a polypeptide, peptide or fragment derived from an allergen so as to interfere with the production of IgE so as to moderate allergic responses to the allergen. The selected antigen may be a polypeptide, peptide or fragment derived from a molecular portion thereof which represents those produced by a host (a self molecule) in an undesired manner, amount or location, such as those from amyloid precursor protein so as to prevent or treat disease characterized by amyloid deposition in a vertebrate host.

In one embodiment of this aspect of the invention, there is provided an immunogenic composition selected comprising a selected antigen as described above with a mutant, immunogenic CT-CRM protein of the invention, and a pharmaceutically acceptable diluent, excipient or carrier.

In still another aspect, this invention provides a method for using these CT-CRMs as adjuvants in immunogenic compositions or methods for increasing the ability of an antigenic composition containing a selected antigen as described above to elicit an immune response in vertebrate host by including an effective adjuvanting amount of one or more of the novel detoxified mutant cholera holotoxins (CT-CRMs) described above.

In yet a further aspect of the invention, there are provided DNA sequences encoding the novel immunogenic, mutant CT-CRMs with substantially reduced toxicity as described above. Preferably, the DNA sequence(s) encodes for both the mutant A subunit with reduced toxicity and subunit B. Alternatively, the DNA sequence may encode only the mutant A subunit with reduced toxicity, where the altered or mutant CT-A is fused with an additional binding domain, or is co-expressed with LT-B and allowed to co-assemble.

In a further aspect of the invention, there is provided a plasmid containing isolated and purified DNA sequence comprising a DNA sequence encoding an immunogenic, detoxified, mutant cholera holotoxin as described herein, and wherein such a DNA sequence is operatively linked to regulatory sequences which direct expression of the CT-CRM in a host cell. Preferably the regulatory sequences comprise an arabinose inducible promoter. In one embodiment of this aspect, the invention relates to a plasmid, designated pLP915, that contains an isolated and purified DNA sequence comprising a DNA sequence encoding an immunogenic mutant CT-CRM with substantially reduced toxicity wherein the amino acid arginine in amino acid position 25 of the A subunit is substituted with an tryptophan. In another embodiment of the invention, the invention relates to a plasmid, designated pLP911, that contains an isolated and purified DNA sequence comprising a DNA sequence encoding an immunogenic mutant CT-CRM with substantially reduced toxicity wherein the amino acid arginine in the amino acid position 25 of the A subunit is substituted with a glycine.

In yet another embodiment of this aspect of the invention, there is provided a plasmid, designated pLP907, that contains an isolated and purified DNA sequence comprising a DNA sequence encoding an immunogenic mutant CT-CRM with substantially reduced toxicity wherein the amino acid residue histidine is inserted in the amino acid position 49 in the A subunit. In still another embodiment of this aspect, the invention relates to a plasmid, designated pLP909, that contains an isolated and purified DNA sequence comprising a DNA sequence encoding an immunogenic, mutant CT-CRM with substantially reduced toxicity wherein the amino acid residues glycine and proline are inserted in the amino acid positions 35 and 36 in the A subunit. In still a further embodiment, the invention relates to a plasmid, designated pLP910, that contains an isolated and purified DNA sequence comprising a DNA sequence encoding an immunogenic, mutant CT-CRM with substantially reduced toxicity wherein the amino acid residue tyrosine in amino acid position 30 of the A subunit is substituted with the amino acid residue tryptophan, and the amino acid residues alanine and histidine are inserted in the amino acid positions 31 and 32 in the A subunit.

In a further aspect of the invention, there is provided a suitable host cell line transformed, infected, transduced or transfected with a plasmid as described herein. The immunogenic, detoxified, mutant cholera holotoxins are produced by transforming, infecting, transducing or transfecting a suitable host cell with one of the plasmids described above and culturing the host cell under culture conditions which permit the expression by the host cell of said recombinant immunogenic, mutant cholera holotoxin protein with substantially reduced toxicity.

These and other aspects of the invention will be apparent to one of skill in the art upon reading of the following detailed description of the invention.

DETAILED DESCRIPTION OF THE INVENTION

Mutant forms of cholera holotoxin that exhibit reduced toxicity, but which retain their superior adjuvanting properties, and the utility of these mutant forms of CTs as adjuvants in immunogenic compositions are described herein.

A. Mutant, Detoxified Cholera Toxin Holotoxins

Novel mutant, detoxified immunogenic forms of cholera holotoxin (CT-CRMs) of this invention are characterized by significantly reduced toxicity compared to a wild-type CT. However, such CT-CRMs retain their ability as powerful stimulators of the immune system. The CT-CRMs of this invention are characterized by one or several amino acid substitutions and/or insertions in the mature CT-A subunit of cholera toxin. The various mutant CT-A subunits of this invention also retained their ability to assemble with CT-B subunits to form mutant CT holotoxins that resembled wild-type CT in adjuvanticity, but which exhibited substantially reduced toxicity compared to the wild-type CT. The CT-CRMs of this invention may employ mutant or altered CT-A subunits associated with wild-type CT-B subunits to create a functional holotoxin. Alternatively, the CT-CRMs of this invention may comprise the altered or mutated CT-A subunits associated with altered or mutated CT-B subunits.

For determination of the amino acid position numbers describing the locations of the amino acid substitutions or insertions in the CT-CRMs of this invention, the sequence of mature CT-A is exemplified as SEQ ID NO: 2, i.e., amino acids 19-258 of SEQ ID NO: 1, a wild-type CT sequence. The nucleotide sequence encoding the A subunit of the cholera holotoxin is set forth in International patent publication No. WO 93/13202. Similarly, a suitable mature CT-B sequence may be illustrated by amino acids 280-382 of SEQ ID NO: 1. However, other variants, biotypes and fragments of CT-A and CT-B of *V. cholerae* may also be employed as sequences containing the amino acid substitutions and insertions described herein. See, for example, the ELTOR biotype of C. Shi et al, 1993 *Sheng Wu Hua Hsueh Tsa Chih*, 9(4):395-399; NCBI database locus No. AAC34728, and other sources of variants of *V. cholerae* toxin.

In one embodiment of this invention, the amino acid substitutions or insertions resulting in some of the CT-CRMs of this invention are the result of replacing one amino acid with another amino acid having similar structural and/or chemical properties, i.e. conservative amino acid replacements. "Conservative" amino acid substitutions or insertions may be made on the basis of similarity in polarity, charge, solubility hydrophobicity, hydrophilicity, and/or the amphipathic nature of the residues involved. For example, non-polar (hydrophobic) amino acids include alanine, leucine, isoleucine, valine, proline, tryptophan, and methionine; polar/neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. This invention is exemplified by CT-CRMs, two bearing a single amino acid substitution, one bearing a single amino acid insertion, one bearing a double amino acid insertion, and one bearing a single amino acid substitution and a double amino acid insertion. These CT-CRMs were generated as described in detail in Example 1 with the following mutations in the A subunit as set forth in Table 1.

TABLE 1

Single and Double CT-CRM Mutants

| Amino Acid Substitution | Native | Mutant | Abbreviation |
|---|---|---|---|
| 25 | Arginine | Tryptophan | CT-CRM$_{R25W}$ |
| 25 | Arginine | Glycine | CT-CRM$_{R25G}$ |
| 48 and 49 | Threonine$_{48}$ | Threonine$_{48}$, Histidine$_{49}$ | CT-CRM$_{T48TH}$ |
| 34, 35, 36 | Glycine$_{34}$ | Glycine$_{34}$, Glycine$_{35}$, Proline$_{36}$ | CT-CRM$_{G34GGP}$ |
| 30, 31, 32 | Tyrosine$_{30}$ | Tryptophan$_{30}$, Alanine$_{31}$, Histidine$_{32}$ | CT-CRM$_{Y30WAH}$ |

Thus, in one embodiment, a novel CT-CRM of this invention comprises the amino acid sequence of CT subunit A or a fragment thereof, wherein the amino acid residue in the amino acid position 25 of the A subunit is substituted with another amino acid which substitution results in a substantial reduction in toxicity. In a preferred embodiment of the invention, the amino acid arginine at amino acid position 25 of the A subunit is substituted with a tryptophan. In another preferred embodiment of the invention, the amino acid arginine at amino acid position 25 of the A subunit is substituted with a glycine. The resulting CT-CRM$_{R25W}$ and CT-CRM$_{R25G}$ each demonstrate superior adjuvanting properties.

A novel CT-CRM of this invention comprises a single amino acid insertion at the amino acid position at the amino acid position adjacent to the amino acid residue at the amino acid position 48 in the A subunit, which insertion results in a substantial reduction of toxicity. In a preferred embodiment of the invention the amino acid histidine is inserted adjacent to the amino acid position 48 in the A subunit, resulting in the mutant CT-CRM$_{T48TH}$, which demonstrates superior adjuvanting properties.

Another novel CT-CRM of this invention comprises a double amino acid insertion in the amino acid positions 35 and 36 adjacent to the amino acid residue at the amino acid position 34, in the A subunit, which insertion results in a substantial reduction of toxicity. In a preferred embodiment of the invention the amino acids glycine and proline are inserted adjacent to the amino acid position glycine 34 in the A subunit, resulting in the mutant CT-CRM$_{G34GGP}$, which demonstrates superior adjuvanting properties.

Yet another novel CT-CRM of this invention comprises a single amino acid substitution at the amino acid position 30 and double amino acid insertion at the amino acid positions 31 and 32 adjacent to the amino acid residue at the amino acid position 30), in the A subunit, which substitution and insertion results in a substantial reduction of toxicity. In a preferred embodiment of the invention, the amino acid residue tyrosine at amino acid position 30 is substituted with the amino acid residue tryptophan and the amino acid residues alanine and histidine are inserted thereafter, resulting in the mutant CT-CRM$_{Y30WAH}$, which demonstrates superior adjuvanting properties.

Still other CT-CRMs of this invention may contain at least the single substitutions or single or double mutations described specifically above and at least one additional mutation at a position other than at one or more of the amino acid residues 25, 30, 31, 32, 34, 35, 36, 48 and 49, as set forth above. International patent publication No. WO 93/13202, which is hereby incorporated by reference, describes a series of mutations in the CT-A subunit that serve to reduce the toxicity of the cholera holotoxin. These mutations include making substitutions for the arginine at amino acid 7, the aspartic acid at position 9, the arginine at position 11, the glutamic acid at position 29, the histidine at position 44, the valine at position 53, the arginine at position 54, the serine at position 61, the serine at position 63, the histidine at position 70, the valine at position 97, the tyrosine at position 104, the proline at position 106, the histidine at position 107, the glutamic acid at position 110, the glutamic acid at position 112, the serine at position 114, the tryptophan at position 127, the arginine at position 146 and the arginine at position 192. International patent publication No. WO 98/42375, which is hereby incorporated by reference, describes making a substitution for the serine at amino acid 109 in the A subunit, which serves to reduce the toxicity of the cholera holotoxin.

Other useful CT-CRM mutant proteins useful in this invention include a full-length holotoxin with one or more of the specific mutations provided above, and a hexameric, CT-CRM polypeptide or a fragment thereof containing the mutagenized residues described above and which protein, polypeptide or fragment retains the adjuvanticity of wild-type CT from which it is derived, but is characterized by reduced toxicity. Immunologically active fragments of these CT-CRMs with reduced enzymatic activity may also be useful in the methods and compositions of this invention. Fragments ordinarily will contain at least at least about 25 contiguous amino acids of the CT-CRM subunit proteins containing the sites of mutagenesis noted above. More typically a CT-CRM subunit fragment contains at least about 75 contiguous amino acids of the A or B subunits. Another fragment of a CT-CRM subunit contains at least about 100 contiguous amino acids of either subunit. Still another embodiment of a CT-CRM CT-A subunit may contain about 150 amino acids or less than 240 amino acids.

A fragment of the CT-CRMs described herein is useful in the methods and compositions described below if it generates or enhances the immune response to selected antigens in the vertebrate host. Fragments include truncations of the carboxy-terminal region of the CT-CRM subunits. For example, a CT-CRM truncated so that it contains only a CT-A mutant subunit is a desirable fragment. Similarly, CT-A subunits truncated at about residues 240 or 250 are desirable fragments. Still other fragments CT-CRMs of this invention may be selected. Additional fragments of the CT-CRM holotoxin may contain less than five repetitions of the CT-B subunits or truncated CT-B subunits. The foregoing fragments may also contain one or more of the specific mutations described above.

Other suitable CT-CRM proteins may include those in which one or more of the amino acid residues includes a substituted group. Still another suitable CT-CRM holotoxin protein is one in which one or more of the subunits of the hexameric CT-CRM protein is fused with another compound, such as a compound to increase the half-life of the molecule (for example, polyethylene glycol). Another suitable CT-CRM protein is one in which additional amino acids are fused to one or more of the polypeptide subunits, such as a leader or secretory sequence, or a sequence which is employed to enhance the immunogenicity of the CT-CRM protein. Still other modifications of the CT-CRMs include the above-mentioned deletion of the CT-A signal or leader sequences at the N terminus of CT, i.e., amino acids 1-18 of SEQ ID NO: 1, and/or the deletion of the CT-B signal or leader sequence, i.e., at amino acids 259-279 of SEQ ID NO: 1, and/or the deletion of other regions that do not effect immunogenicity. Similarly, a modification of the CT-CRMs described herein includes include replacing either signal or leader sequences with other signal or leader sequences. See, e.g., U.S. Pat. No. 5,780,601, incorporated by reference herein.

Still another example of suitable CT-CRM proteins are those in which optional amino acids (e.g., -Gly-Ser-) or other amino acid or chemical compound spacers may be included at the termini of the polypeptide subunits for the purpose of lining multiple holotoxin proteins together or to a carrier. For example, useful CT-CRMs may include one or more of the above-described CT-CRMs or subunits thereof coupled to a carrier protein. Alternatively, a useful CT-CRM may be present in a fusion protein containing multiple CT-CRMs, optionally coupled to carrier protein.

For these embodiments, the carrier protein is desirably a protein or other molecule that can enhance the immunogenicity of the selected CT-CRM. Such a carrier may be a larger molecule that also has an adjuvanting effect. Exemplary conventional protein carriers include, without limitation, E. coli DnaK protein, galactokinase (GalK, which catalyzes the first step of galactose metabolism in bacteria), ubiquitin, α-mating factor, β-galactosidase, and influenza NS-1 protein. Toxoids (i.e., the sequence which encodes the naturally occurring toxin, with sufficient modifications to eliminate its toxic activity) such as diphtheria toxoid and tetanus toxoid, their respective toxins, and any mutant forms of these proteins, such as $CRM_{197}$ (a non-toxic form of diphtheria toxin, see U.S. Pat. No. 5,614,382), may also be employed as carriers. Other carriers include exotoxin A of Pseudomonas aeruginosa, heat labile toxins of E. coli and rotaviral particles (including rotavirus and VP6 particles). Alternatively, a fragment or epitope of the carrier protein or other immunogenic protein may be used. For example, a hapten may be coupled to a T cell epitope of a bacterial toxin. See U.S. Pat. No. 5,785,973. Similarly a variety of bacterial heat shock proteins, e.g., mycobacterial hsp-70 may be used. Glutathione-S-transferase (GST) is another useful carrier. One of skill in the art can readily select an appropriate carrier for use in this context. The fusion proteins may be formed by standard techniques for coupling proteinaceous materials. Fusions may be expressed from fused gene constructs prepared by recombinant DNA techniques as described below.

Other suitable CT-CRMs described herein can differ from the specifically exemplified CT-CRMs by modifications that do not revive enzymatic toxicity, and do not diminish adjuventicity, or by combinations of such attributes. Preferably, the amino acid substitutions are the result of replacing one amino acid with another amino acid having similar structural and/or chemical properties, i.e. conservative amino acid replacements. "Conservative" amino acid substitutions may be made on the basis of similarity in polarity, charge, solubility hydrophobicity, hydrophilicity, and/or the amphipathic nature of the residues involved. For example, non-polar (hydrophobic) amino acids include alanine, leucine, isoleucine, valine, proline, tryptophan, and methionine; polar/neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

For example, conservative amino acid changes may be made, which, although they alter the primary sequence of the subunits of the CT-CRM protein, do not normally alter the function of the molecule. In making such changes, the hydropathic index of amino acids can be considered. The importance of the hydropathic amino acid index in conferring interactive biologic function on a polypeptide is generally understood in the art (Kyte & Doolittle, 1982, J. Mol. Biol., 157(1):105-32). It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid residue determines the secondary and tertiary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within +/−2 is preferred, those within +/−1 are particularly preferred, and those within +/−0.5 are even more particularly preferred.

Substitution or insertion of like amino acids can also be made on the basis of hydrophilicity, particularly where the biologically functional equivalent polypeptide or peptide thereby created is intended for use in immunological embodiments. U.S. Pat. No. 4,554,101, incorporated herein by reference, states that the greatest local average hydrophilicity of a polypeptide, as governed by the hydrophilicity of its adjacent amino acids, correlates with its immunogenicity and antigenicity, i.e. with a biological property of the polypeptide. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred; those within ±1 are particularly preferred; and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

In addition, modifications, which do not normally alter the primary sequence of the CT-CRM protein, include in vivo or in vitro chemical derivatization of polypeptides, e.g., acetylation, methylation, or carboxylation. Also included as CT-CRMs of this invention are these proteins modified by glycosylation, e.g., those made by modifying the glycosylation patterns of a polypeptide during its synthesis and processing or in further processing steps; or by exposing the polypeptide to enzymes which affect glycosylation, such as mammalian glycosylating or deglycosylating enzymes. Also embraced as CT-CRMs are the above-identified mutagenized sequences, which have phosphorylated amino acid residues, e.g., phosphotyrosine, phosphoserine, or phosphothreonine.

Also included as CT-CRMs of this invention are the above sequences that have been modified using ordinary molecular biological techniques so as to improve their resistance to proteolytic degradation or to optimize solubility properties. Among such CT-CRMs are included those containing residues other than naturally occurring L-amino acids, e.g., D-amino acids or non-naturally occurring synthetic amino acids. Among other known modifications which may be present in CT-CRMs of the present invention are, without limitation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, GPI anchor formation, hydroxylation, iodination, methylation, myristoylation, oxidation, proteolytic processing, prenylation, racemization, selenoylation, sulfation, transfer-RNA mediated addition of amino acids to proteins such as arginylation, and ubiquitination.

The phenotypic effects of the novel CT-CRMs of Table 1 on the structure and function of CT were assessed. The mutant A subunits with either a single amino acid substitution, a single amino acid insertion, a double amino acid insertion or a single amino acid substitution and double amino acid insertion, generated by site directed mutagenesis of the CT-encoding gene were also able to assemble with CT-B subunits into immunoreactive holotoxin in the presence of subunit B as determined by non-denaturing gel electrophoresis assay (see Table 2, Example 2). Each mutant holotoxin was also tested in a Y-1 adrenal tumor cell assay to determine its residual toxicity compared to wild-type CT holotoxin (see Tables 3 and 4, Example 3). These holotoxins resembled wild-type CT in their adjuvanticities, but the results presented in Table 3 demonstrate that the mutant CT-CRMs had substantially reduced toxicity when compared with wild-type cholera holotoxin. The residual toxicity of the CT-CRMs with single and double amino acid substitutions were substantially reduced in comparison to that of the wild-type CT. These data demonstrate that the mutant CT-CRMs are holotoxins and are substantially less toxic than wild-type CT. Specifically, the mutant CT-CRMs displayed significantly lower levels of toxicity than the wild-type cholera holotoxin in the Y-1 mouse adrenal cell assay.

Each of the mutant CT-CRMs was also compared to wild-type CT in an ADP-ribosyltransferase activity assay (see Example 4). The results, which were generally in agreement with the toxicity data generated in the Y-1 adrenal cell assay, indicated that the ADP-ribosyltransferase activity of the various CT-CRMs was substantially reduced when compared to wild-type CT (Tables 5 and 6).

As used herein, the terms and phrases "the holotoxin has reduced toxicity" or "substantially less toxic" or the like mean that the CT-CRM mutant of this invention, such as the five CT-CRM mutants described herein (CT-CRM$_{R25W}$, CT-CRM$_{R25G}$, CT-CRM$_{T48TH}$, CT-CRM$_{G34GGP}$, CT-CRM$_{Y30WAH}$), exhibits a substantially lower toxicity per unit of purified toxin protein compared to the wild-type CT. This "reduced toxicity" enables each mutant to be used as an adjuvant in an immunogenic composition without causing significant side effects, particularly those known to be associated with CT, e.g., diarrhea. As described in more detail below, the mutant CT-CRMs of this invention display significantly lower levels of toxicity than the wild-type CT in the Y-1 mouse adrenal cell assay, and a significantly reduced ADP-ribosyltransferase activity when compared to wild-type CT.

The immunogenic mutant CT-CRMs according to the present invention exhibit a balance of reduced toxicity and retained adjuvanticity, such that the resulting mutant CT protein functions as an adjuvant while being tolerated safely by the vertebrate host to which it is introduced. As indicated in the examples below, results in murine model assay systems indicate that the mutant CT-CRMs disclosed herein were able to significantly augment mucosal and systemic immune responses following intranasal administration of disparate antigens. Furthermore, even in the presence of pre-existing anti-CT immune responses, the mutant CT-CRMs were able to serve as efficient mucosal adjuvants. The studies that support these characteristics of the CT-CRMs of this invention are summarized below and more specifically stated in the Examples.

To evaluate the efficacy of the mutant CT-CRMs as mucosal adjuvants for compositions containing bacterial or viral antigens that have been identified as candidates for inclusion in immunogenic compositions, two disparate model antigen systems were examined: (1) the recombinant P4 outer membrane protein (also known as protein "e"(rP4)) of the nontypable *Haemophilus influenzae* bacterium (NTHi), (see U.S. Pat. No. 5,601,831), and (2) the native UspA2 outer membrane protein of the *Moraxella catarrhalis* bacterium (International Patent Publication No. WO 98/28333).

Importantly, the data demonstrate that the mutant CT-CRMs are able to augment mucosal and systemic immune responses following intranasal (IN) administration of disparate antigens. Results in murine model systems indicate that all mutant CT-CRMs disclosed herein were able to significantly augment mucosal and systemic immune responses following intranasal administration of these disparate antigens. Furthermore, even in the presence of pre-existing anti-CT immune responses, the mutant CT-CRMs were able to serve as efficient mucosal adjuvants (see Tables 6-18).

The immunogenic mutant CT-CRMs according to the present invention exhibit a balance of reduced toxicity and retained adjuvanticity, such that the protein functions as an adjuvant while being tolerated safely by the vertebrate host immunized with the composition.

B. Nucleic Acid Molecules Encoding CT-CRMs

Another aspect of this invention includes isolated, synthetic or recombinant nucleic acid molecules and sequences encoding the above-described CT-CRMs and/or subunits thereof having the specified site directed mutations, substitutions and/or insertions, or fragments that may further contain one or more of those mutations, substitutions and/or insertions.

An isolated nucleotide molecule comprising a nucleic acid sequence encoding a CT-CRM protein may be preferably under the control of regulatory sequences that direct expression of the CT-CRM in a host cell. As described herein, such nucleic acid molecules may be used to express the CT-CRM protein in vitro or to permit expression of the CT-CRM protein in vivo in a human.

As used herein, the term "isolated nucleotide molecule or sequence" refers to a nucleic acid segment or fragment which is free from contamination with, other biological components that may be associated with the molecule or sequence in its natural environment. For example, one embodiment of an isolated nucleotide molecule or sequence of this invention is a sequence separated from sequences which flank it in a naturally occurring state, e.g., a DNA fragment which has been removed from the sequences which are normally adjacent to the fragment, such as the sequences adjacent to the fragment in a genome in which it naturally occurs. Further, the nucleotide sequences and molecules of this invention have been altered to encode a CT-CRM protein of this invention. Thus, the term "isolated nucleic acid molecule or sequence" also applies to nucleic acid sequences or molecules that have been substantially purified from other components that naturally accompany the unmutagenized nucleic acid, e.g., RNA or DNA or proteins, in the cell. An isolated nucleotide molecule or sequence of this invention also encompasses sequences and molecules that have been prepared by other conventional methods, such as recombinant methods, synthetic methods, e.g., mutagenesis, or combinations of such methods. The nucleotide sequences or molecules of this invention should not be construed as being limited solely to the specific nucleotide sequences presented herein, but rather should be construed to include any and all nucleotide sequences which share homology (i.e., have sequence identity) with the nucleotide sequences presented herein.

The terms "substantial homology" or "substantial similarity," when referring to a nucleic acid or fragment thereof, indicate that, when optimally aligned with appropriate nucleotide insertions or deletions with another nucleic acid (or its complementary strand), there is nucleotide sequence identity in at least about 70% of the nucleotide bases, as measured by any well-known algorithm of sequence identity, such as FASTA, a program in GCG Version 6.1. The term "homologous" as used herein, refers to the sequence similarity between two polymeric molecules, e.g., between two nucleic acid molecules, e.g., two DNA molecules or two RNA molecules, or between two polypeptide molecules. When a nucleotide or amino acid position in both of the two molecules is occupied by the same monomeric nucleotide or amino acid, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous, then the two sequences are 50% homologous. If 90% of the positions, e.g., 9 of 10, are matched or homologous, the two sequences share 90% homology. By way of example, the DNA sequences 3'ATTGCC5' and 3'TATGCG5' share 50% homology. By the term "substantially homologous" as used herein, is meant DNA or RNA which is about 70% homologous, more preferably about 80% homologous, and most preferably about 90% homologous to the desired nucleic acid.

The invention is also directed to an isolated nucleotide molecule comprising a nucleic acid sequence that is at least 70%, 80% or 90% homologous to a nucleic acid sequence encoding a CT-CRM protein or subunit of this invention that has reduced enzymatic toxicity compared to wild-type CT protein and that retains adjuvanticity of the wild-type CT. Furthermore, due to the degeneracy of the genetic code, any three-nucleotide codon that encodes a mutant or substituted amino acid residue of CT-CRM, described herein is within the scope of the invention.

Where, as discussed herein, CT-CRMs, mutant CT-A subunits, or mutant CT-B subunits, and/or DNA sequences encoding them, or other sequences useful in nucleic acid molecules or compositions described herein are defined by their percent homologies or identities to identified sequences, the algorithms used to calculate the percent homologies or percent identities include the following: the Smith-Waterman algorithm (J. F. Collins et al, 1988, *Comput. Appl. Biosci.,* 4:67-72; J. F. Collins et al, Molecular Sequence Comparison and Alignment, (M. J. Bishop et al, eds.) In Practical Approach Series: Nucleic Acid and Protein Sequence Analysis XVIII, IRL Press: Oxford, England, UK (1987) pp. 417), and the BLAST and FASTA programs (E. G. Shpaer et al, 1996, *Genomics,* 38:179-191). These references are incorporated herein by reference.

By describing two DNAs as being "operably linked" as used herein, is meant that a single-stranded or double-stranded DNA comprises each of the two DNAs and that the two DNAs are arranged within the DNA in such a manner that at least one of the DNA sequences is able to exert a physiological effect by which it is characterized upon the other.

Preferably, for use in producing a CT-CRM protein of this invention or in administering it for in vivo production in a cell, each CT-CRM protein encoding sequence and necessary regulatory sequences are present in a separate viral or non-viral recombinant vector (including non-viral methods of delivery of a nucleic acid molecule into a cell). Alternatively, two or more of these nucleic acid sequences encoding duplicate copies of a CT-CRM protein or encoding multiple different CT-CRMs of this invention may be contained in a polycistronic transcript, i.e., a single molecule designed to express multiple gene products.

The invention further relates to vectors, particularly plasmids, containing isolated and purified DNA sequences comprising DNA sequences that encode an immunogenic mutant cholera holotoxin. Desirable embodiments include plasmids containing DNA sequences which encode, for example, an immunogenic mutant cholera holotoxin having single amino acid substitutions at amino acid residue 25 of CT-A, a single amino acid insertion between amino acid residues 48 and 49 of CT-A, double amino acid insertions between amino acid residues 34 and 35 of CT-A, or a single amino acid substitution at amino acid residues 30 and a double amino acid insertion between amino acids 30 and 31 of CT-A By the term "vector" as used herein, is meant a DNA molecule derived from viral or non-viral, e.g., bacterial, species that has been designed to encode an exogenous or heterologous nucleic acid sequence. Thus, the term includes conventional bacterial plasmids. Such plasmids or vectors can include plasmid sequences from viruses or phages. Such vectors include chromosomal, episomal and virus-derived vectors, e.g., vectors derived from bacterial plasmids, bacteriophages, yeast episomes, yeast chromosomal elements, and viruses. Vectors may also be derived from combinations thereof, such as those derived from plasmid and bacteriophage genetic elements, cosmids, and phagemids. The term also includes non-replicating viruses that transfer a gene from one cell to another. The term should also be construed to include non-plasmid and non-viral compounds which facilitate transfer of nucleic acid into cells, such as, for example, polylysine compounds and the like.

The nucleic acid molecules of the invention include non-viral vectors or methods for delivery of the sequences encoding the CT-CRM protein to a host cell according to this invention. A variety of non-viral vectors are known in the art and may include, without limitation, plasmids, bacterial vectors, bacteriophage vectors, "naked" DNA and DNA condensed with cationic lipids or polymers.

Examples of bacterial vectors include, but are not limited to, sequences derived from *bacille Calmette Guérin* (BCG), *Salmonella, Shigella, E. coli*, and *Listeria*, among others. Suitable plasmid vectors include, for example, pBR322, pBR325, pACYC177, pACYC184, pUC8, pUC9, pUC18, pUC19, pLG339, pR290, pK37, pKC101, pAC105, pVA51, pKH47, pUB110, pMB9, pBR325, Col E1, pSC101, pBR313, pML21, RSF2124, pCR1, RP4, pBAD18, and pBR328.

Examples of suitable inducible *Escherichia coli* expression vectors include pTrc (Amann et al., 1988 *Gene*, 69:301-315), the arabinose expression vectors (e.g., pBAD18, Guzman et al, 1995 *J. Bacteriol.*, 177:4121-4130), and pETIId (Studier et al., 1990 *Methods in Enzymology*, 185:60-89). Target gene expression from the pTrc vector relies on host RNA polymerase transcription from a hybrid trp-lac fusion promoter. Target gene expression from the pETIId vector relies on transcription from a T7 gn10-lac fusion promoter mediated by a coexpressed viral RNA polymerase T7 gn 1. This viral polymerase is supplied by host strains BL21 (DE3) or HMS I 74(DE3) from a resident prophage harboring a T7 gn1 gene under the transcriptional control of the lacUV5 promoter. The pBAD system relies on the inducible arabinose promoter that is regulated by the araC gene. The promoter is induced in the presence of arabinose.

As one example, a plasmid, designated pLP9911, contains an isolated and purified DNA sequence comprising a DNA sequence encoding an immunogenic mutant CT-CRM with substantially reduced toxicity having a single amino acid substitution (arginine to tryptophan) at amino acid position 25 in the A subunit (CT-$CRM_{R25W}$). As another example, a plasmid, designated pLP9915, contains an isolated and purified DNA sequence comprising a DNA sequence encoding an immunogenic mutant CT-CRM with substantially reduced toxicity having a single amino acid substitution (arginine to glycine) at amino acid position 25 in the A subunit (CT-$CRM_{R25G}$). A third plasmid, designated pLP9907, contains an isolated and purified DNA sequence comprising a DNA sequence encoding an immunogenic mutant CT-CRM with substantially reduced toxicity wherein a single amino acid histidine is inserted at the amino acid position 49 adjacent to the amino acid residue threonine at the amino acid position 48 in the A subunit (CT-$CRM_{T48TH}$). Another exemplary plasmid is designated pLP9909. This plasmid contains an isolated and purified DNA sequence comprising a DNA sequence encoding an immunogenic, mutant CT-CRM with substantially reduced toxicity wherein a double amino acid insertion of amino acid residues glycine and proline is inserted in the amino acid positions 35 and 36 adjacent to the amino acid residue glycine at the amino acid position 34 in the A subunit (CT-$CRM_{G34GGP}$). Another plasmid exemplified in this invention is designated pLP9910. It contains an isolated and purified DNA sequence comprising a DNA sequence encoding an immunogenic, mutant CT-CRM with substantially reduced toxicity wherein a single amino acid substitution at the amino acid position 30 (substitution of the amino acid residue tyrosine at amino acid position 30 with amino acid residue tryptophan) and a double amino acid insertion of amino acid residues (alanine and histidine) in the amino acid positions 31 and 32 adjacent to the amino acid residue at the amino acid position 30 are made in the A subunit (CT-$CRM_{Y30WAH}$).

Another type of useful vector is a single or double-stranded bacteriophage vector. For example, a suitable cloning vector includes, but is not limited to the vectors such as bacteriophage λ vector system, λgt11, μgt μWES.tB, Charon 4, λgt-WES-λB, Charon 28, Charon 4A, λgt-1-λBC, λgt-1-λB, M13 mp7, M13 mp8, or M13 mp9, among others.

In another embodiment, the expression vector is a yeast expression vector. Examples of vectors for expression in a yeast such as *S. cerevisiae* include pYepSec I (Baldari, et al., 1987 *Protein Eng.*, 1(5):433-437), pMFa (Kurjan and Herskowitz, 1982 *Cell*, 30(3):933-943), pJRY88 (Schultz et al., 1987 *Gene*, 61(2): 123-133), and pYES2 (Invitrogen Corporation, San Diego, Calif.).

Alternatively, baculovirus expression vectors are used. Baculovirus vectors available for expression of proteins in cultured insect cells (e.g., Sf 9 or Sf 21 cells) include the pAc series (Smith et al., 1983 *Biotechnol.*, 24:434-443) and the pVL series (Luckow and Summers, 1989 *Virol.*, 170(1):31-39).

In yet another embodiment, a mammalian expression vector is used for expression in mammalian cells. Examples of mammalian expression vectors include pCDM8 (Seed, 1987 *Nature*, 329:840-842) and pMT2PC (Kaufman et al., 1987 *EMBO J.*, 6(1):187-93). When used in mammalian cells, the expression vector's control functions are often provided by viral regulatory elements.

One type of recombinant vector is a recombinant single or double-stranded RNA or DNA viral vector. A variety of viral vector systems are known in the art. Examples of such vectors include, without limitation, recombinant adenoviral vectors, herpes simplex virus (HSV)-based vectors, adeno-associated viral (AAV) vectors, hybrid adenoviral/AAV vectors, recombinant retroviruses or lentiviruses, recombinant poxvirus vectors, recombinant vaccinia virus vectors, SV-40 vectors, insect viruses such as baculoviruses, and the like that are constructed to carry or express a selected nucleic acid composition of interest.

Retrovirus vectors that can be employed include those described in EP 0 415 731; International Patent Publication Nos. WO 90/07936; WO 94/03622; WO 93/25698; and WO 93/25234; U.S. Pat. No. 5,219,740; International Patent Publication Nos. WO 93/11230 and WO 93/10218; Vile and Hart, 1993 *Cancer Res.* 53:3860-3864; Vile and Hart, 1993 *Cancer Res.* 53:962-967; Ram et al., 1993 *Cancer Res.* 53:83-88; Takamiya et al., 1992 *J. Neurosci. Res.* 33:493-503; Baba et al., 1993 *J. Neurosurg.* 79:729-735; U.S. Pat. No. 4,777,127; GB Patent No. 2,200,651; and EP 0 345 242. Examples of suitable recombinant retroviruses include those described in International Patent Publication No. WO 91/02805.

Alphavirus-based vectors may also be used as the nucleic acid molecule encoding the CT-CRM protein. Such vectors can be constructed from a wide variety of alphaviruses, including, for example, Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532). Representative examples of such vector systems include those described in U.S. Pat. Nos. 5,091,309; 5,217,879; and 5,185,440; and International Patent Publication Nos. WO 92/10578; WO 94/21792; WO 95/27069; WO 95/27044; and WO 95/07994.

Examples of adenoviral vectors include those described by Berkner, 1988 *Biotechniques* 6:616-627; Rosenfeld et al., 1991 *Science* 252:431-434; International Patent Publication No. WO 93/19191; Kolls et al., 1994 *PNAS* 91:215-219; Kass-Eisler et al., 1993 *PNAS* 90:11498-11502; Guzman et al., 1993 *Circulation* 88:2838-2848; Guzman et al., 1993 *Cir. Res.* 73:1202-1207; Zabner et al., 1993 *Cell* 75:207-216; Li et al., 1993 *Hum. Gene Ther.* 4:403-409; Cailaud et al., 1993 *Eur. J. Neurosci.* 5:1287-1291; Vincent et al., 1993 *Nat. Genet.* 5:130-134; Jaffe et al., 1992 *Nat. Genet.* 1:372-378; and Levrero et al., 1991 *Gene* 101: 195-202. Exemplary adenoviral vectors include those described in International Patent Publication Nos. WO 94/12649; WO 93/03769; WO 93/19191; WO 94/28938; WO 95/11984 and WO 95/00655. Other adenoviral vectors include those derived from chimpanzee adenoviruses, such as those described in U.S. Pat. No. 6,083,716.

Another viral vector is based on a parvovirus such as an adeno-associated virus (AAV). Representative examples include the AAV vectors described in International Patent Publication No. WO 93/09239, Samulski et al., 1989 *J. Virol.* 63:3822-3828; Mendelson et al., 1988 *Virol.* 166:154-165; and Flotte et al., 1993 *PNAS* 90:10613-10617. Other particularly desirable AAV vectors include those based upon AAV1; see, International Patent Publication No. WO 00/28061, published May 18, 2000. Other desirable AAV vectors include those which: are pseudotyped, i.e., contain a minigene composed of AAV 5' ITRs, a transgene, and AAV 3' ITRs packaged in a capsid of an AAV serotype heterologous to the AAV ITRs. Methods of producing such pseudotyped AAV vectors are described in detail in International Patent Publication No. WO01/83692.

In an embodiment in which the nucleic acid molecule of the invention is "naked DNA", it may be combined with polymers including traditional polymers and non-traditional polymers such as cyclodextrin-containing polymers and protective, interactive noncondensing polymers, among others. The "naked" DNA and DNA condensed with cationic lipids or polymers are typically delivered to the cells using chemical methods. A number of chemical methods are known in the art for cell delivery and include using lipids, polymers, or proteins to complex with DNA, optionally condensing the same into particles, and delivering to the cells. Another non-viral chemical method includes using cations to condense DNA, which is then placed in a liposome and used according to the present invention. See, C. Henry, 2001 *Chemical and Engineering News,* 79(48):35-41.

The nucleic acid molecule encoding the CT-CRM of this invention is introduced directly into the cells either as "naked" DNA (U.S. Pat. No. 5,580,859) or formulated in compositions with agents that facilitate immunization, such as bupivicaine and other local anesthetics (U.S. Pat. No. 6,127,170).

All components of the viral and non-viral vectors above may be readily selected from among known materials in the art and available from the pharmaceutical industry. Selection of the vector components and regulatory sequences are not considered a limitation on this invention. Each nucleic acid sequence encoding a CT-CRM protein according to this invention is preferably under the control of regulatory sequences that direct the replication and generation of the product of each nucleic acid sequence in a mammalian or vertebrate cell. By the term "promoter/regulatory sequence" is meant a DNA sequence required for expression of a nucleic acid operably linked thereto. Preferably the promoter/regulatory sequence is positioned at the 5' end of the coding sequence such that it drives expression of the CT-CRM protein in a cell. In some instances, the promoter/regulatory sequence may function in a tissue specific manner. For example, the promoter/regulatory sequence is only capable of driving expression in a cell of a particular tissue type. In some instances, this sequence may be the core promoter sequence and in other instances, this sequence may also include an enhancer sequence and other regulatory elements that are required for expression in a tissue-specific manner.

Suitable promoters may be readily selected from among constitutive promoters, inducible promoters, tissue-specific promoters and others. Examples of constitutive promoters that are non-specific in activity and employed in the nucleic acid molecules encoding the CT-CRM protein of this invention include, without limitation, the retroviral Rous sarcoma virus (RSV) promoter, the retroviral LTR promoter (optionally with the RSV enhancer), the cytomegalovirus (CMV) promoter (optionally with the CMV enhancer) (see, e.g., Boshart et al, *Cell,* 41:521-530 (1985)), the SV40 promoter, the dihydrofolate reductase promoter, the β-actin promoter, the phosphoglycerol kinase (PGK) promoter, and the EF1α promoter (Invitrogen).

Inducible promoters that are regulated by exogenously supplied compounds, include, without limitation, the arabinose promoter, the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al, 1996 *Proc. Natl. Acad. Sci. USA,* 93:3346-3351), the tetracycline-repressible system (Gossen et al, 1992 *Proc. Natl. Acad. Sci. USA,* 89:5547-5551), the tetracycline-inducible system (Gossen et al, 1995 *Science,* 268:1766-1769, see also Harvey et al, 1998 *Curr. Opin. Chem Biol,* 2:512-518), the RU486-inducible system (Wang et al, 1997 *Nat. Biotech.,* 15:239-243 and Wang et al, 1997 *Gene Ther.,* 4:432-441) and the rapamycin-inducible system (Magari et al, 1997 *J. Clin. Invest.,* 100: 2865-2872). A particularly preferred promoter for use in expression systems for CT-CRMs is an arabinose inducible promoter.

Other types of inducible promoters that may be useful in this context are those regulated by a specific physiological state, e.g., temperature or acute phase or in replicating cells only. Useful tissue-specific promoters include the promoters from genes encoding skeletal β-actin, myosin light chain 2A, dystrophin, muscle creatine kinase, as well as synthetic muscle promoters with activities higher than naturally-occurring promoters (see Li et al., 1999 *Nat. Biotech.,* 17:241-245). Examples of promoters that are tissue-specific are known for liver (albumin, Miyatake et al. 1997 *J. Virol.,* 71:5124-32; hepatitis B virus core promoter, Sandig et al., 1996 *Gene Ther.,* 3: 1002-9; alpha-fetoprotein (AFP), Arbuthnot et al., 1996 *Hum. Gene Ther.,* 7:1503-14), bone (osteocalcin, Stein et al., 1997 *Mol. Biol. Rep.,* 24:185-96; bone sialoprotein, Chen et al., 1996 *J. Bone Miner. Res.,* 11:654-64), lymphocytes (CD2, Hansal et al., 1988 *J. Immunol.,* 161:1063-8; immunoglobulin heavy chain; T cell receptor α chain), neuronal (neuron-specific enolase (NSE) promoter, Andersen et al. 1993 *Cell. Mol. Neurobiol.,* 13:503-15; neurofilament light-chain gene, Piccioli et al., 1991 *Proc. Natl. Acad. Sci. USA,* 88:5611-5; the neuron-specific ngf gene, Piccioli et al., 1995 *Neuron,* 15:373-84); among others. See, e.g., International Patent Publication No. WO00/55335 for additional lists of known promoters useful, in this context.

Additional regulatory sequences for inclusion in a nucleic acid sequence, molecule or vector of this invention include, without limitation, an enhancer sequence, a polyadenylation sequence, a splice donor sequence and a splice acceptor sequence, a site for transcription initiation and termination positioned at the beginning and end, respectively, of the polypeptide to be translated, a ribosome binding site for translation in the transcribed region, an epitope tag, a nuclear localization sequence, an IRES element, a Goldberg-Hogness "TATA" element, a restriction enzyme cleavage site, a selectable marker and the like. Enhancer sequences include, e.g., the 72 bp tandem repeat of SV40 DNA or the retroviral long terminal repeats or LTRs, etc. and are employed to increase transcriptional efficiency. Selection of promoters and other common vector elements are conventional and many such sequences are available with which to design the nucleotide molecules and vectors useful in this invention. See, e.g., Sambrook et al, *Molecular Cloning. A Laboratory Manual,* Cold Spring Harbor Laboratory, New York, (1989) and references cited therein at, for example, pages 3.18-3.26 and 16.17-16.27 and Ausubel et al., *Current Protocols in Molecular Biology*, John Wiley & Sons, New York (1989). One of skill in the art may readily select from among such known regulatory sequences to prepare molecules of this invention. The selection of such regulatory sequences is not a limitation of this invention.

C. Methods for Making the CT-CRM Proteins and Nucleotide Molecules of this Invention In view of the demonstrated utility of mutant CT-CRMs as adjuvants for antigenic compositions, production of suitable quantities of mutant CT-CRMs is desirable. The preparation or synthesis of the nucleotide sequences and CT-CRMs, as well as compositions containing the nucleotide molecules or CT-CRM protein of this invention disclosed herein is well within the ability of the person having ordinary skill in the art using available material. The synthesis methods are not a limitation of this invention. The examples below detail presently preferred embodiments of synthesis of sequences encoding the CT-CRMs of this invention.

The CT-CRMs and nucleotide molecules and sequences of this invention may be produced by chemical synthesis methods, recombinant genetic engineering methods, site directed mutagenesis, among others, and combinations of such methods. For example, the nucleotide sequences/CT-CRMs of the invention may be prepared conventionally by resort to known chemical synthesis techniques, e.g., solid-phase chemical synthesis, such as described by Merrifield, 1963 *J. Amer. Chem. Soc.,* 85:2149-2154; J. Stuart and J. Young, Solid Phase Peptide Synthesis, Pierce Chemical Company, Rockford, Ill. (1984); Matteucci et al., 1981 *J. Am. Chem. Soc.,* 103:3185; Alvarado-Urbina et al., 1980 *Science,* 214:270; and Sinha, N. D. et al., 1984 *Nucl. Acids Res.,* 13:4539, among others. See, also, e.g., PROTEINS—STRUCTURE AND MOLECULAR PROPERTIES, 2nd Ed., T. E. Creighton, W. H. Freeman and Company, New York, 1993; Wold, F., "Posttranslational Protein Modifications: Perspectives and Prospects", pgs. 1-12 in POST-TRANSLATIONAL COVALENT MODIFICATION OF PROTEINS, B. C. Johnson, Ed., Academic Press, New York, 1983; Seifter et al, 1990 *Meth. Enzymol.,* 182:626-646, and Rattan et al, 1992 *Ann. N.Y. Acad. Sci.,* 663:48-62.

Alternatively, compositions of this invention may be constructed recombinantly using conventional molecular biology techniques, site-directed mutagenesis, genetic engineering or polymerase chain reaction, such as, by cloning and expressing a nucleotide molecule encoding a CT-CRM protein with optional other immunogens and optional carrier proteins within a host microorganism, etc. utilizing the information provided herein (See, e.g., Sambrook et al., cited above; Ausubel et al. cited above). Coding sequences for the CT-CRMs and optional immunogens can be prepared synthetically (W. P. C. Stemmer et al, 1995 *Gene,* 164:49).

In general, recombinant DNA techniques involve obtaining by synthesis or isolation a DNA sequence that encodes the CT-CRM protein as described above, and introducing it into an appropriate vector/host cell expression system where it is expressed preferably under the control of an arabinose inducible promoter. Any of the methods described for the insertion of DNA into an expression vector may be used to ligate a promoter and other regulatory control elements into specific sites within the selected recombinant vector. Suitable host cells are then transformed, infected, transduced or transfected with such vectors or plasmids by conventional techniques.

A variety of host cell-vector (plasmid) systems may be used to express the immunogenic mutant cholera holotoxin. The vector system, which preferably includes the arabinose inducible promoter, is compatible with the host cell used. The DNA encoding the mutant CT-CRMs are inserted into an expression system, and the promoter (preferably the arabinose inducible promoter), and other control elements are ligated into specific sites within the vector so that when the vector is inserted into a host cell (by transformation, transduction or transfection, depending on the host cell-vector system used) the DNA encoding the CT-CRM is expressed by the host cell.

The vector may be selected from one of the viral vectors or non-viral vectors described above but must be compatible with the host cell used. The recombinant DNA vector may be introduced into appropriate host cells (bacteria, virus, yeast, mammalian cells or the like) by transformation, transduction or transfection (depending upon the vector/host cell system). Host-vector systems include but are not limited to bacteria transformed with bacteriophage DNA, plasmid DNA or cosmid DNA; microorganisms such as yeast containing yeast vectors; mammalian cell systems infected with virus (e.g., vaccinia virus, adenovirus, etc.); and insect cell systems infected with virus (e.g., baculovirus).

Systems for cloning and expressing the CT-CRMs and other compositions of this invention using the synthetic nucleic acid molecules include the use of various microorganisms and cells that are well known in recombinant technology. The host cell may be selected from any biological organism, including prokaryotic (e.g., bacterial) cells and eukaryotic cells, including, mammalian, insect cells, yeast cells. Preferably, the cells employed in the various methods and compositions of this invention are bacterial cells. Suitable bacterial cells include, for example, various strains of *E. coli, Bacillus,* and *Streptomyces.* Yeast cells such as *Saccharomyces* and *Pichia,* and insect cells such as Sf9 and Sf21 cells are also useful host cells for production purposes. Mammalian cells including but not limited to Chinese hamster ovary cells (CHO), chick embryo fibroblasts, baby hamster kidney cells, NIH3T3, PER C6, NSO, VERO or COS cells are also suitable host cells, as well as other conventional and non-conventional organisms and plants.

The selection of other suitable host cells and methods for transformation, culture, amplification, screening and product production and purification can be performed by one of skill in the art by reference to known techniques. See, e.g., Gething and Sambrook, 1981 Nature, 293:620-625, among others.

Typically, the host cell is maintained under culture conditions for a period of time sufficient for expression. Culture conditions are well known in the art and include ionic composition and concentration, temperature, pH and the like. Typically, transfected cells are maintained under culture conditions in a culture medium Suitable media for various cell types are well known in the art. In a preferred embodiment, temperature is from about 20° C. to about 50° C., more preferably from about 30° C. to about 40° C. and, even more preferably about 37° C.

The pH is preferably from about a value of 6.0 to a value of about 8.0, more preferably from about a value of about 6.8 to a value of about 7.8 and, most preferably about 7.4. Osmolality is preferably from about 200 milliosmols per liter (mosm/L) to about 400 mosm/l and, more preferably from about 290 mosm/L to about 310 mosm/L. Other biological conditions needed for transfection and expression of an encoded protein are well known in the art.

Recombinant CT-CRM protein is recovered or collected either from the host cells or membranes thereof or from the medium in which those cells are cultured. Recovery comprises isolating and purifying the recombinant CT-CRM protein. Isolation and purification techniques for polypeptides are well known in the art and include such procedures as precipitation, filtration, chromatography, electrophoresis and the like.

When produced by conventional recombinant means, CT-CRMs of this invention may be isolated and purified from the cell or medium thereof by conventional methods, including chromatography (e.g., ion exchange, affinity, and sizing column chromatography), centrifugation, differential solubility, or by any other standard techniques for the purification or proteins. Several techniques exist for purification of heterologous protein from prokaryotic cells. See, U.S. Pat. Nos. 4,518,526; 4,599,197; and 4,734,362. The purified preparation however produced should be substantially free of host toxins, which might be harmful to humans. In particular, when expressed in gram negative bacterial host cells such as $E\ coli$, the purified peptide or protein should be substantially free of endotoxin contamination. See, e.g., Sambrook et al., cited above.

The CT-CRMs used in methods and compositions of the invention are not limited to products of any of the specific exemplary processes listed herein. In fact, the protein may be prepared by the methods in the texts cited immediately above or by methods of the texts cited elsewhere in this specification It is within the skill of the art to isolate and produce recombinantly or synthetically protein compositions for such use.

The five exemplary CT-CRMs of Table 1, two bearing a single amino acid substitution, one bearing a single amino acid insertion, and two bearing double amino acid substitutions were generated as described in detail in Example 1 using some of the methods described above. Specifically, a set of mutant CT clones (CT-CRMs) were generated in $E.\ coli$ by standard site-directed mutagenesis protocols on plasmids encoding the known CT holotoxin molecules. It has previously been shown that the resulting yield of purified CT-CRM$_{E29H}$ holotoxin was approximately 50 µg per liter of culture medium (see International patent publication No. WO 00/18434). Initial attempts to increase CT-CRM$_{E29H}$ yield via modifications to the original plasmid, showed little or no effect. A moderate increase in yield was achieved through co-expression of the plasmid pIIB29H, and derivatives, with Vibrio cholerae DsbA and $E.\ coli$ RpoH. Co-expression and purification modifications increased the yield of CT-CRM$_{E29H}$ to approximately 2 mg/liter.

In order to increase the expression of CT-CRMs of the present invention, the lactose inducible promoter in the plasmids was replaced with an arabinose inducible promoter (Invitrogen Corporation, Carlsbad, Calif.), which was operatively linked to the DNA sequence encoding the CT-CRMs. During cloning it was determined that plasmid pIIB29H contained a ctxA gene encoding CT subunit A from Vibrio cholerae strain 569B, linked to a ctxB gene encoding CT subunit B from Vibrio cholerae strain 2125. Cross alignment of these genes indicated seven base substitutions between the two ctxB genes and a single base change between the ctxA genes. Several of these base substitutions led to amino acid changes in the mature subunits. Of special note is the substitution between the ctxA genes which leads to an amino acid change within the A-2 portion, or the holotoxin assembly domain of the A subunit. It was not known whether the heterogeneity between these genes had a negative impact on toxin expression or holotoxin assembly. However, it was thought preferable from an evolutionary standpoint that both toxin subunit genes originate from the same source. As such, both the ctxA and ctxB genes used in the construction of the arabinose inducible system originated from Vibrio cholerae strain 569B. The construction of plasmids pLP911, pLP915, pLP907, pLP909 and pLP910 is described in Example 1. The immunogenic mutant cholera holotoxin is produced by transforming, infecting, transducing or transfecting a host cell with a plasmid described above, and culturing the host cell under conditions that permit the expression of said recombinant immunogenic detoxified protein by the host cell. The yield of CT-CRMs from pLP911, pLP915, pLP907, pLP909 and pLP910 is approximately 7.6, 5.6, 7.9, 27.4, and 1.9 mg of purified material per liter of culture, respectively.

The resulting CT-CRM protein or nucleic acid molecule may be formulated into an immunogenic composition with any number of selected antigens and screened for adjuvant efficacy by in vivo assays, such as those described in the examples below.

D. Immunogenic Compositions

An effective immunogenic composition according to the invention is one comprising a mutant cholera holotoxin of this invention. Preferably the mutant cholera holotoxin CT-CRM has reduced toxicity compared to a wild-type cholera holotoxin. This "reduced toxicity" enables each mutant to be used as an adjuvant in an immunogenic composition without causing significant side effects, particularly those known to be associated with wild-type CT, e.g., diarrhea. More preferably, the CT-CRM in the immunogenic composition of this invention has a single amino acid substitution (arginine to tryptophan or arginine to glycine) at amino acid position 25 in the A subunit (CT-CRM$_{R25W}$, CT-CRM$_{R25G}$). In another preferred embodiment, the CT-CRM has a single amino acid insertion of histidine in the amino acid position 49 adjacent to the amino acid residue threonine at the amino acid position 48 in the A subunit (CT-CRM$_{T48TH}$). A third preferred embodiment is a CT-CRM with a double amino acid insertion of amino acid residues glycine and proline in the amino acid positions 35 and 36 adjacent to the amino acid residue glycine at the amino acid position 34 in the A subunit (CT-CRM$_{G34GGP}$). A fourth exemplary CT-CRM has a single amino acid substitution at the amino acid position 30 (tyrosine for tryptophan) and a double amino acid insertion of amino acid residues alanine and histidine in the amino acid positions 31 and 32 adjacent to the amino acid residue at the amino acid position 30 in the A subunit (CT-CRM$_{Y30WAH}$). In one embodiment, the CT-CRM may have one or more additional modifications as described above. In another embodiment, the composition comprises a selected antigen and a suitable effective adjuvanting amount of the CT-CRM, wherein said holotoxin significantly enhances the immune response in a vertebrate host to said antigen. The compositions of the present invention modulate the immune response by improving the vertebrate host's antibody response and cell-mediated immune responses to the administration of a composition comprising a selected antigen as described above.

As used herein, the term "effective adjuvanting amount" means a dose of one of the CT-CRM mutants of this invention that is effective in eliciting an increased immune response in a vertebrate host. In a more specific definition, the term "effective adjuvanting amount" means a dose of one of the five CT-CRM mutants described herein (CT-CRM$_{R25W}$, CT-CRM$_{R25G}$, CT-CRM$_{T48TH}$, CT-CRM$_{G34GGP}$, CT-CRM$_{Y30WAH}$), effective in eliciting an increased immune response in a vertebrate host. Specifically, the CT-CRMs disclosed herein augment mucosal and systemic immune responses following intranasal administration of disparate antigens. Furthermore, even in the presence of pre-existing anti-CT immune responses, the mutant CT-CRMs were able to serve as efficient mucosal adjuvants. The immunogenic mutant CT-CRMs according to the present invention exhibit a balance of reduced toxicity and retained adjuvanticity, such that the resulting mutant CT protein functions as an adjuvant while being tolerated safely by the vertebrate host to which it is introduced. The particular "effective adjuvanting dosage or amount" will depend upon the age, weight and medical condition of the host, as well as on the method of administration Suitable doses are readily determined by persons skilled in the art.

The immunogenic compositions containing as an adjuvant the mutant cholera holotoxins of this invention also contain at least one antigen selected from among a wide variety of antigens. The antigen(s) may comprise a whole cell or virus, or one or more saccharides, proteins, protein subunits, polypeptide, peptide or fragments, poly- or oligo-nucleotides, or other macromolecular components. If desired, the antigenic compositions may contain more than one antigen from the same or different pathogenic microorganisms.

Thus, in one embodiment, the immunogenic compositions of this invention comprise as the selected antigen a polypeptide, peptide or fragment derived from a pathogenic bacterium. Desirable bacterial immunogenic compositions including the CT-CRM mutant(s) as an adjuvant include those directed to the prevention and/or treatment of disease(s) caused by, without limitation, *Haemophilus influenzae* (both typable and nontypable), *Haemophilus somnus, Moraxella catarralis, Streptococcus pneumoniae, Streptococcus pyogenes, Streptococcus agalactiae, Streptococcus faecalis, Helicobacter pylori, Neisseria meningitidis, Neisseria gonorrhoeae, Chlamydia trachomatis, Chlamydia pneumoniae, Chlamydia psittaci, Bordetella pertussis, Alloiococcus otiditis, Salmonella typhi, Salmonella typhimurium, Salmonella choleraesuis, Escherichia coli, Shigella, Vibrio cholerae, Corynebacterium diphtheriae, Mycobacterium tuberculosis, Mycobacterium avium-Mycobacterium intracellulare* complex, *Proteus mirabilis, Proteus vulgaris, Staphylococcus aureus, Staphylococcus epidermidis, Clostridium tetani, Leptospira interrogans, Borrelia burgdorferi, Pasteurella haemolytica, Pasteurella multocida, Actinobacillus pleuropneumoniae* and *Mycoplasma gallisepticum.*

In another embodiment, the immunogenic compositions of this invention comprise as the selected antigen a polypeptide, peptide or fragment derived from a pathogenic virus. Desirable viral immunogenic compositions including the CT-CRM mutant(s) as an adjuvant include those directed to the prevention and/or treatment of disease caused by, without limitation, Respiratory syncytial virus, Parainfluenza virus types 1-3, Human metapneumovirus, Influenza virus, Herpes simplex virus, Human cytomegalovirus, Human immunodeficiency virus, Simian immunodeficiency virus, Hepatitis A v Hepatitis B virus, Hepatitis C virus, Human papillomavirus, Poliovirus, rotavirus, caliciviruses, Measles virus, Mumps virus, Rubella virus, adenovirus, rabies virus, canine distemper virus, rinderpest virus, avian pneumovirus (formerly turkey rhinotracheitis virus), Hendra virus, Nipah virus, coronavirus, parvovirus, infectious rhinotracheitis viruses, feline leukemia virus, feline infectious peritonitis virus, avian infectious bursal disease virus, Newcastle disease virus, Marek's disease virus, porcine respiratory and reproductive syndrome virus, equine arteritis virus and various Encephalitis viruses.

In another embodiment, the immunogenic compositions of this invention comprise as the selected antigen a polypeptide, peptide or fragment derived from a pathogenic fungus. Desirable immunogenic compositions against fungal pathogens including the CT-CRM mutant(s) as an adjuvant include those directed to the prevention and/or treatment of disease(s) caused by, without limitation, *Aspergillis, Blastomyces, Candida, Coccidiodes, Cryptococcus* and *Histoplasma.*

In still another embodiment, the immunogenic compositions of this invention comprise as the selected antigen a polypeptide, peptide or fragment derived from a pathogenic parasite. Desirable immunogenic compositions against parasites including the CT-CRM mutant(s) as an adjuvant include those directed to the prevention and/or treatment of disease(s) caused by, without limitation, *Leishmania major, Ascaris, Trichuris, Giardia, Schistosoma, Cryptosporidium, Trichomonas, Toxoplasma gondii* and *Pneumocystis carinii.*

Desirable immunogenic compositions directed against non-infectious diseases including the CT-CRM mutant(s) as an adjuvant are also within the scope of this invention. Such immunogenic compositions include those directed to vertebrate antigens, particularly compositions directed against antigens for the prevention and/or treatment of disease(s), without limitation, such as allergy, autoimmune disease, Alzheimer disease and cancer.

For example, the immunogenic composition of this invention may contain a polypeptide, peptide or fragment derived from a cancer cell or tumor cell. Desirable immunogenic compositions for eliciting a therapeutic or prophylactic anti-cancer effect in a vertebrate host, which contain the CT-CRM mutants of this invention, include those utilizing a cancer antigen or tumor-associated antigen including, without limitation, prostate specific antigen, carcino-embryonic antigen, MUC-1, Her2, CA-125, MAGE-3, hormones, hormone analogs and so forth.

Other immunogenic compositions of this invention are desirable for moderating responses to allergens in a vertebrate host. Such compositions contain the CT-CRM mutant(s) of this invention and a polypeptide, peptide or fragment derived from an allergen or fragment thereof. Examples of such allergens are described in the U.S. Pat. No. 5,830,877 and International patent publication No. WO 99/51259, which are hereby incorporated by reference, and include pollen, insect venoms, animal dander, fungal spores and drugs (such as penicillin). The immunogenic compositions interfere with the production of IgE antibodies, a known cause of allergic reactions, so as to moderate allergic responses to the allergen.

In still another embodiment, the immunogenic compositions of this invention contain as the selected antigen a polypeptide, peptide or fragment derived from a molecular portion of an antigen, which represents those produced by a host (a self molecule) in an undesired manner, amount or location, such as those from amyloid precursor protein so as to prevent or treat disease characterized by amyloid deposition in a vertebrate host. Desirable compositions for moderating responses to self molecules in a vertebrate host, which contain CT-CRM mutants of this invention, include those containing a self molecule or fragment thereof. Examples of such self molecules include β-chain insulin involved in diabetes, the G17 molecule involved in gastroesophageal reflux disease, and antigens which downregulate autoimmune responses in diseases such as multiple sclerosis, lupus and rheumatoid arthritis.

Still other immunogenic compositions of this invention are desirable for preventing or treating disease characterized by amyloid deposition in a vertebrate host. Such compositions contain the CT-CRM mutant(s) of this invention as well as portions of amyloid precursor protein (APP). This disease is referred to variously as Alzheimer's disease, amyloidosis or amyloidogenic disease. The β-amyloid precursor protein (also referred to as Aβ peptide) is a 42 amino acid fragment of APP, which is generated by processing of APP by the β and γ secretase enzymes, and has the following sequence: Asp Ala Glu Phe Arg His Asp Ser Gly Tyr Glu Val His His Gln Lys Leu Val Phe Phe Ala Glu Asp Val Gly Ser Asn Lys Gly Ala Ile Ile Gly Leu Met Val Gly Gly Val Val Ile Ala (SEQ ID NO: 3). In some patients, the amyloid deposit takes the form of an aggregated Aβ peptide. Surprisingly, it has now been found that administration of isolated Aβ peptide induces an immune response against the Aβ peptide component of an amyloid deposit in a vertebrate host (International patent publication No. WO 99/27944). Thus, embodiments of this invention include the CT-CRM mutants of this invention plus Aβ peptide, as well as fragments of Aβ peptide and antibodies to Aβ peptides or fragments thereof. One such fragment of Aβ peptide is the 28 amino acid peptide having the following sequence (U.S. Pat. No. 4,666,829): Asp Ala Glu Phe Arg His Asp Ser Gly Tyr Glu Val His His Gln Lys Leu Val Phe Phe Ala Glu Asp Val Gly Ser Asn Lys (SEQ ID NO: 4).

Such immunogenic compositions further comprise an immunologically acceptable diluent or a pharmaceutically acceptable carrier, such as sterile water or sterile isotonic saline. The antigenic compositions may also be mixed with such diluents or carriers in a conventional manner. As used herein the language "pharmaceutically acceptable carrier" is intended to include any and all solvents, dispersion media, coatings, antibacterial and antifungal agents, isotonic and absorption delaying agents, and the like, compatible with administration to humans or other vertebrate hosts. The appropriate carrier will be evident to those skilled in the art and will depend in large part upon the route of administration.

The immunogenic compositions may also include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i e., powder or granular) form for reconstitution with a suitable vehicle (e.g., sterile pyrogen-free water) prior to parenteral administration of the reconstituted composition. Other parenterally-administrable formulations, which are useful, include those, which comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

Still additional components that may be present in the protein immunogenic compositions of this invention are adjuvants in addition to the CT-CRMs, preservatives, chemical stabilizers, or other antigenic proteins. Typically, stabilizers, adjuvants, and preservatives are optimized to determine the best formulation for efficacy in the target human or animal. Suitable exemplary preservatives include chlorobutanol, potassium sorbate, sorbic acid, sulfur dioxide, propyl gallate, the parabens, ethyl vanillin, glycerin, phenol, and parachlorophenol. Suitable stabilizing ingredients that may be used include, for example, casamino acids, sucrose, gelatin, phenol red, N-Z amine, monopotassium diphosphate, lactose, lactalbumin hydrolysate, and dried milk.

The antigenic compositions of this invention may comprise further adjuvants in addition to the mutant CT-CRMs. Conventional non-CT-CRM adjuvants used to enhance an immune response include, without limitation, MPL™ (3-O-deacylated monophosphoryl lipid A; Corixa, Hamilton, Mont.), which is described in U.S. Pat. No. 4,912,094, which is hereby incorporated by reference. Also suitable for use as adjuvants are synthetic lipid A analogs or aminoalkyl glucosamine phosphate compounds (AGP), or derivatives or analogs thereof, which are available from Corixa (Hamilton, Mont.), and which are described in U.S. Pat. No. 6,113,918, which is hereby incorporated by reference. One such AGP is 2-[(R)-3-Tetradecanoyloxytetradecanoylamino]ethyl 2-Deoxy-4-O-phosphono-3-O-[(R)-3-tetradecanoyoxytetradecanoyl]-2-[(R)-3-tetradecanoyoxytetradecanoylamino]-b-D-glucopyranoside, which is also known as 529 (formerly known as RC529). This 529 adjuvant is formulated as an aqueous form or as a stable emulsion.

Still other non-CT-CRM adjuvants include mineral oil and water emulsions, aluminum salts (alum), such as aluminum hydroxide, aluminum phosphate, etc., Amphigen, Avridine, L121/squalene, D-lactide-polylactide/glycoside, pluronic polyols, muramyl dipeptide, killed *Bordetella,* saponins, such as Stimulon™ QS-21 (Antigenics, Framingham, Mass.), described in U.S. Pat. No. 5,057,540, which is hereby incorporated by reference, and particles generated therefrom such as ISCOMS (immunostimulating complexes), *Mycobacterium tuberculosis*, bacterial lipopolysaccharides, synthetic polynucleotides such as oligonucleotides containing a CpG motif (U.S. Pat. No. 6,207,646, which is hereby incorporated by reference), a pertussis toxin (PT), or an *E. coli* heat-labile toxin (LT), particularly LT-K63, LT-R72, CT-S109, PT-K9/G129; see, e.g., International Patent Publication Nos. WO 93/13302 and WO 92/19265, incorporated herein by reference.

Various cytokines and lymphokines are also suitable for inclusion in the immunogenic compositions of this invention. One such cytokine is granulocyte-macrophage colony stimulating factor (GM-CSF), which has a nucleotide sequence as described in U.S. Pat. No. 5,078,996, which is hereby incorporated by reference. A plasmid containing GM-CSF cDNA has been transformed into *E. coli* and has been deposited with the American Type Culture Collection (ATCC), 10801 University Boulevard, Manassas, Va. 20110-2209, under Accession Number 39900. The cytokine Interleukin-12 (IL-12) is another adjuvant that is described in U.S. Pat. No. 5,723,127, which is hereby incorporated by reference (available from Genetics Institute, Inc., Cambridge, Mass.). Other cytokines or lymphokines have been shown to have immune modulating activity, including, but not limited to, the interleukins 1-$\alpha$, 1-$\beta$, 2, 4, 5, 6, 7, 8, 10, 13, 14, 15, 16, 17 and 18, the interferons-$\alpha$, $\beta$ and $\gamma$, granulocyte colony stimulating factor, and the tumor necrosis factors $\alpha$ and $\beta$, and are suitable for use as adjuvants.

Still other suitable optional components of the immunogenic compositions of this invention include, but are not limited to: surface active substances (e.g., hexadecylamine, octadecylamine, octadecyl amino acid esters, lysolecithin, dimethyl-dioctadecylammonium bromide), methoxyhexadecylgylcerol, and pluronic polyols; polyamines, e.g., pyran, dextransulfate, poly IC, carbopol; peptides, e.g., muramyl dipeptide, dimethylglycine, tuftsin; oil emulsions; and mineral gels, e.g., aluminum phosphate, etc. and immune stimulating complexes. The CT-CRM and antigen may also be incorporated into liposomes, or conjugated to polysaccharides, lipopolysaccharides and/or other polymers for use in an immunogenic composition.

Immunogenic compositions of this invention including the CT-CRM mutant(s), or DNA sequences and molecules encoding the desired CT-CRM of this invention, are also useful as polynucleotide compositions (also known as DNA immunogenic compositions) or administered with polynucleotides encoding the selected antigen. For example, it has been previously demonstrated that BALB/c mice administered a formulation of plasmid DNA (pDNA) encoding the full length glycoprotein D of herpes simplex virus (HSV) type 2 (gD2), along with CT-CRM$_{E29H}$ by the intradermal route generated a higher average cellular response than those that received plasmid DNA encoding HSV gD2 by itself by the intradermal route. In addition, the average serum antibody titers for mice, which, received the plasmid DNA HSV gD2 composition along with CT-CRM$_{E29H}$ was approximately the same as that seen in mice that received the plasmid DNA HSV gD2 composition without adjuvant. Similarly, the plasmid DNA HSV gD2 composition adjuvanted with CT-CRM$_{E29H}$ also generated a gD2-specific antibody response in vaginal wash samples at levels that were comparable to those seen following the delivery of the non-adjuvanted composition by intradermal or intramuscular routes. Mice immunized with the plasmid DNA HSV gD2 composition adjuvanted with CT-CRM$_{E29H}$ or CT and delivered by the intradermal route also generated substantially higher levels of gamma interferon and IL-5 than mice that received the plasmid DNA HSV-gD2 composition without adjuvant. Thus, CT-CRMs enhance proliferative and gamma interferon responses when administered with a plasmid DNA composition against HSV.

In addition to a carrier as described above, immunogenic compositions composed of polynucleotide molecules desirably contain optional polynucleotide facilitating agents or "co-agents", such as a local anesthetic, a peptide, a lipid including cationic lipids, a liposome or lipidic particle, a polycation such as polylysine, a branched, three-dimensional polycation such as a dendrimer, a carbohydrate, a cationic amphiphile, a detergent, a benzylammonium surfactant, or another compound that facilitates polynucleotide transfer to cells. Such a facilitating agent includes bupivicaine (see U.S. Pat. No. 5,593,972, which is hereby incorporated by reference). Other non-exclusive examples of such facilitating agents or co-agents useful in this invention are described in U.S. Pat. Nos. 5,703,055; 5,739,118; 5,837,533; International Patent Publication No. WO96/10038, published Apr. 4, 1996; and International Patent Publication No WO94/16737, published Aug. 8, 1994, which are each incorporated herein by reference.

Most preferably, the local anesthetic is present in an amount that forms one or more complexes with the nucleic acid molecules. When the local anesthetic is mixed with nucleic acid molecules or plasmids of this invention, it forms a variety of small complexes or particles that pack the DNA and are homogeneous. Thus, in one embodiment of the immunogenic compositions of this invention, the complexes are formed by mixing the local anesthetic and at least one plasmid of this invention. Any single complex resulting from this mixture may contain a variety of combinations of the different plasmids. Alternatively, in another embodiment of the compositions of this invention, the local anesthetic may be pre-mixed with each plasmid separately, and then the separate mixtures combined in a single composition to ensure the desired ratio of the plasmids is present in a single immunogenic composition, if all plasmids are to be administered in a single bolus administration. Alternatively, the local anesthetic and each plasmid may be mixed separately and administered separately to obtain the desired ratio. Where, hereafter, the term "complex" or "one or more complexes" or "complexes" is used to define this embodiment of the immunogenic composition, it is understood that the term encompasses one or more complexes with each complex containing a mixture of the CT-CRM-encoding plasmids and antigen-encoding plasmids, or a mixture of complexes formed discretely, wherein each complex contains only one type of plasmid, or a one or a mixture of complexes wherein each complex contains a polycistronic DNA Preferably, the complexes are between about 50 to about 150 nm in diameter. When the facilitating agent used is a local anesthetic, preferably bupivacaine, an amount of from about 0.1 weight percent to about 1.0 weight percent based on the total weight of the polynucleotide composition is preferred. See, also, International Patent Publication No. WO99/21591, which is hereby incorporated by reference, and which teaches the incorporation of benzylammonium surfactants as co-agents, preferably administered in an amount of between about 0.001-0.03 weight %. According to the present invention, the amount of local anesthetic is present in a ratio to said nucleic acid molecules of 0.01-2.5% w/v local anesthetic to 1-10 μg/ml nucleic acid. Another such range is 0.05-1.25% w/v local anesthetic to 100 μg/ml to 1 ml/ml nucleic acid.

As used, such a polynucleotide immunogenic composition expresses the CT-CRM and antigens on a transient basis in vivo; no genetic material is inserted or integrated into the chromosomes of the host. This use is thus distinguished from gene therapy, where the goal is to insert or integrate the genetic material of interest into the chromosome. An assay is used to confirm that the polynucleotides administered by immunization do not rise to a transformed phenotype in the host (U.S. Pat. No. 6,168,918).

The immunogenic compositions may also contain other additives suitable for the selected mode of administration of the composition. The composition of the invention may also involve lyophilized polynucleotides, which can be used with other pharmaceutically acceptable excipients for developing powder, liquid or suspension dosage forms. See, e.g., Remington: The Science and Practice of Pharmacy, Vol. 2, 19$^{th}$ edition (1995), e.g., Chapter 95 Aerosols; and International Patent Publication No. WO99/45966, the teachings of which are hereby incorporated by reference. Routes of administration for these compositions may be combined, if desired, or adjusted.

These nucleic acid molecule-containing immunogenic compositions can contain additives suitable for administration via any conventional route of administration. In some preferred embodiments, the immunogenic composition of the invention is prepared for administration to human subjects in the form of, for example, liquids, powders, aerosols, tablets, capsules, enteric-coated tablets or capsules, or suppositories.

The immunogenic compositions of the present invention (whether protein-containing or nucleic acid molecule-containing compositions), as described above, are not limited by the selection of the conventional, physiologically acceptable, carriers, adjuvants, or other ingredients useful in pharmaceutical preparations of the types described above. The preparation of these pharmaceutically acceptable compositions, from the above-described components, having appropriate pH isotonicity, stability and other conventional characteristics is within the skill of the art.

E. Methods of Use of the Compositions of this Invention

The immunogenic compositions of this invention that comprise the CT-CRM alone or a combination of the CT-CRM and a selected antigen, are administered to a human or to a non-human vertebrate by a variety of routes to enhance the immune response to an antigen, preferably a disease-causing antigen, as identified above. The compositions of the present invention modulate the immune response by improving the vertebrate host's antibody response and cell-mediated immunity after administration of a composition comprising a selected antigen as described above, and an effective adjuvanting amount of a mutant CT-CRM, where the mutant CT-CRM has substantially reduced toxicity compared to a wild-type CT, and wherein the reduced toxicity is a result of a single amino acid substitution, a single amino acid insertion, a double amino acid insertion or a single amino acid substitution and double amino acid insertion.

In one embodiment, the immunogenic composition containing the CT-CRM (either as a protein or encoded by a nucleic acid molecule) is administered prior to administration of a composition comprising the selected antigen (either as a protein or as a nucleic acid). In another embodiment, the immunogenic composition is administered simultaneously with the antigen, whether it is administered in a composition containing both antigen and CT-CRM or as a separate composition from that of the antigen-containing composition. In still a further embodiment, the composition containing the CT-CRM is administered after the composition containing the antigen. It is preferable, although not required, that the antigen and the mutant CT-CRM be administered at the same time.

The immunogenic composition containing the CT-CRM may be administered as a protein or as a nucleic acid molecule encoding the protein, as described above. The immunogenic composition containing the CT-CRM may be administered as a protein in combination with a selected antigen administered as a protein. Alternatively, as described above, the CT-CRM immunogenic composition may be administered as a protein with a nucleic acid molecule encoding the antigen, as described above. Still another alternative involves administering both the CT-CRM and the antigen as nucleic acid sequences encoding these proteins.

Any suitable route of administration may be employed to administer the immunogenic composition containing the CT-CRM. The route may be the same or different from a route selected to administer a composition containing the selected antigen, if the CT-CRM and antigen are administered in separate compositions or in different forms, e.g., protein or nucleic acids. Suitable routes of administration include, but are not limited to, intranasal, oral, vaginal, rectal, parenteral, intradermal, transdermal (see, e.g., International patent publication No. WO 98/20734, which is hereby incorporated by reference), intramuscular, intraperitoneal, subcutaneous, intravenous and intraarterial. The appropriate route is selected depending on the nature of the immunogenic composition used, and an evaluation of the age, weight, sex and general health of the patient and the antigens present in the immunogenic composition, and similar factors by an attending physician.

In general, selection of the appropriate "effective amount" or dosage for the the CT-CRM and/or antigen components of the immunogenic composition(s) of the present invention will also be based upon the protein or nucleic acid form of the CT-CRM and antigen, the identity of the antigen in the immunogenic composition(s) employed, as well as the physical condition of the subject, most especially including the general health, age and weight of the immunized subject. The method and routes of administration and the presence of additional components in the immunogenic compositions may also affect the dosages and amounts of the CT-CRM and antigen. Such selection and upward or downward adjustment of the effective dose is within the skill of the art. The amount of CT-CRM and antigen required to induce an immune response, preferably a protective response, or produce an exogenous effect in the patient without significant adverse side effects varies depending upon these factors. Suitable doses are readily determined by persons skilled in the art.

As an example, in one embodiment, for the compositions containing protein components, e.g., a CT-CRM variant protein and/or antigen as described above, each dose may comprise between about 1 μg to about 20 mg of the protein per mL of a sterile solution. Other dosage ranges may also be contemplated by one of skill in the art. Initial doses may be optionally followed by repeated boosts, where desirable.

In another example, the amounts of nucleotide molecules in the DNA and vector compositions may be selected and adjusted by one of skill in the art. In one embodiment, each dose will comprise between about 50 μg to about 1 mg of CT-CRM-encoding or antigen-encoding nucleic acid, e.g., DNA plasmid, per mL of a sterile solution.

The number of doses and the dosage regimen for the composition are also readily determined by persons skilled in the art. Protection may be conferred by a single dose of the immunogenic composition containing the CT-CRM, or may require the administration of several doses with or without the selected antigen, in addition to booster doses at later times to maintain protection. In some instances, the adjuvant property of the mutant CT-CRM may reduce the number of doses containing antigen that are needed or may reduce the time course of the dosage regimen. The levels of immunity can be monitored to determine the need, if any, for boosters.

In order that this invention may be better understood, the following examples are set forth. The examples are for the purpose of illustration only and are not to be construed as limiting the scope of the invention.

All references cited herein are hereby incorporated by reference.

EXAMPLE 1

Expression of CT Mutants

A. Bacterial Strains, Plasmids and Growth Conditions.

*E. coli* TG1 (Amersham Corporation, Arlington Heights, Ill.), TX1, a naladixic-acid resistant derivative of TG1 carrying F'Tc, lacI$^q$ from XL1blue (Stratagene, La Jolla, Calif.), TE1 (TG1 ends, F'Tc, lacI$^q$) and CJ236(F'Tc, lacI$^q$) (BioRad, Hercules, Calif.) were used as hosts for cloning recombinant plasmids and expression of variant proteins. Plasmid-containing strains were maintained on LB agar plates with antibiotics as required (ampicillin, 50 μg/ml; kanamycin 25 μg/ml; tetracycline 10 μg/ml).

B. Mutagenesis of ctxA Gene.

Site-directed mutagenesis using single-stranded uracil-containing templates (Jobling, M. G. and Holmes, R. K., 1992 *Infect. Immun.*, 60:4915-24) was used to select for oligonucleotide-derived mutants created in plasmid pMGJ67, a clone of the native CT operon in pSKII- (Stratagene). Briefly, each oligonucleotide was phosphorylated and used to direct second strand synthesis on a single-stranded DNA template rescued from dut ung CJ236 (F'Tc, pMGJ67). Following ligation and transformation of ung$^+$ strain TX1, single-stranded DNA was rescued from Ap$^R$ transformants and sequenced by the dideoxy chain termination method (Kunkel, T. A., 1985 *Proc. Natl. Acad., Sci., USA*, 82:488-492). Some mutations were introduced directly into pARCT2 using the QuickChange mutagenesis method (Stratagene). pARCT2 is an arabinose-inducible clone derived from pAR3 (International Patent Publication No. WO98/20734) expressing an operon containing the ctxA and ctxB genes with signal sequences derived from the LTIIb B gene, and with each gene independently using the translation inititation sequences derived from T7 gene 10 from vector plasmid pT7-7, a derivative of pT7-1.

C. One and Two Codon Insertion Mutations.

Single codon insertions were generated at DdeI restriction sites by partial digestion of pMGJ64 (a derivative of pMGJ67), followed by filling-in of the 3-base sticky ends and self-ligation. Two codon TAB-linker insertion mutations were made by adding six base-pair ApaI linkers (GGGCCC) to the ends of RsaI partial digests of pMGJ64 as described in the TAB manual (Pharmacia). Transformants were screened for loss of either a single DdeI or RsaI site (and presence of a new ApaI site) and confirmed by DNA sequencing.

D. Construction of Arabinose Promoted CT-CRM Expression Vectors.

Previous experience with CT-CRM$_{E29H}$ (International Patent Publication No. WO 00/18434) has shown that maximal production in *E. coli* could be achieved by substituting synthetic Shine-Delgaro sequences upstream of the ctxA gene and placing the operon under the control of the arabinose promoter system. CT operons containing site directed mutations in the A subunit were made as previously described (supra). CT-CRMs were originally under the control of a β-galactosidase promoter and expression levels in *E. coli* were low. PCR was used to modify the region 5' to the ATG of the CT-A subunit and insert an NheI site at the 5' end. The corresponding 3' primer added a HindIII site at the 3' end of the CT-B gene. Primer sequences used were:

```
CT29FNhe:
5' TTTTTTGGGCTAGCATGGAGGAAAAGATGAGC(SEQ ID NO: 5)

CT29RHnd:
5' CGAGGTCGAAGCTTGCATGTTTGGGC.     (SEQ ID NO: 6)
```

PCR was performed on each mutant CT-CRM operon and the PCR products were ligated into pCR2.1-Topo (Invitrogen) according to the manufacturer's directions and transformed into Top10F' cells. Recombinant *E. coli* were plated onto SOB agar containing Kanamycin (25 μg/ml) and X-gal (40 μg/ml). Plasmids from white colonies were screened for inserts by digestion with EcoRI. Plasmids containing inserts of the correct size were digested with NheI and HindIII according to the manufacturer's directions and the DNA fragments containing the CT operons isolated from low melting point agarose. Plasmid pBAD 18-Cm (Invitrogen) was digested with NheI-HindIII and the linear DNA isolated from low melting point agarose. Digested pBAD18 and the CT operons were ligated at 12° C. and transformed into Top10F *E. coli*. Plasmids from chloramphenicol-resistant colonies were screened for inserts by restriction analysis, and representative clones were sequenced to confirm the presence of the site directed mutations. Plasmids were transformed into DH5α for expression of CT-CRMs.

E. Expression of CT-CRMs in *E. coli*.

*E. coli* DH5α cells containing plasmids pLP9911, pLP915, pLP907, pLP909 and pLP910, cells expressing the CT-CRMs respectively, were grown m phosphate buffered Hy-Soy media containing chloramphenicol (25 μg/ml) and glycerol (0.5%) at 37° C. with aeration. When cultures reached an OD$_{600}$ of approximately 4.5-5.5, they were induced by addition of L-arabinose to a final concentration of 0.5%. Cultures were incubated at 37° C. with aeration for three hours post-induction and then the cells collected by centrifugation. Cell pellets were stored at −20° C.

F Preparation and Purification of CT-CRMs.

Cell pellets were thawed at room temperature and resuspended in 10 mM NaPO$_4$ and 1 mM EDTA (pH 7.0) at 9% of the original culture volume. Cell suspensions were mechanically disrupted in a microfluidizer and centrifuged for 10 minutes at 8,500×g. Cell lysates were further clarified at 160,000×g for one hour. The clarified cell lysate was loaded, at a flow rate of 2 ml/minute, onto a carboxymethyl (CM)-sepharose™ column (300 ml CM-Sepharose™ per 10 liters of culture) (Amersham, Pharmacia) equilibrated with 10 mM NaPO$_4$ (pH 7.0). The column was washed with >10 volumes of 10 mM NaPO$_4$ (pH 7.0) at a flow rate of 5 ml/minute. CT-CRM$_{E29H}$ holotoxin was eluted with four column volumes of 10 mM NaPO$_4$ (pH 8.3). Purified CT-CRMs were buffer exchanged by dialysis into PBS and stored at 4° C. The presence of intact holotoxin and the respective subunits was determined by native polyacrylamide gel electrophoresis (PAGE) and SDS-PAGE, respectively. Native PAGE indicated the presence of a purified molecule of 86 kDa (data not shown), the expected molecular weight for intact cholera holotoxin (Tebbey et al, 2000 *Vaccine*, 18(24):2723-2734). In addition, SDS-PAGE showed two bands that aligned with the CT-A (27 kDa) and CT-B (12 kDa) subunits that comprise the intact holotoxin (data not shown).

EXAMPLE 2

Non-Denaturing Polyacrylamide Gel Electrophoresis

Mutant CT-CRMS, CT-CRM$_{R25W}$, CT-CRM$_{R25G}$, CT-CRM$_{T48TH}$, CT-CRM$_{G34GGP}$ and CT-CRM$_{Y30WAH}$, were analyzed by non-denaturing page electrophoresis to determine the percentage of the CT-CRMs present after purification as intact holotoxin. Purified CT-CRMs, 15 μl each (at various protein concentrations), were run through a 6% polymerized non-denaturing polyacrylamide gel. Three different concentrations (300, 600 and 1200 ng) of CT-B were used as a standard. After electrophoresis the gel was stained with Coomassie blue. The gel was then scanned using a densitometer, and the percentage of the holotoxin was calculated from the densitometer readings of the CT-CRMs and CT-B standard. The data indicated that 95% of CT-CRM$_{R25W}$, 91.20% of CT-CRM$_{R25G}$, 91.00% of CT-CRM$_{T48TH}$, 98.80% of CT-CRM$_{G34GGP}$ and 90.93% of CT-CRM$_{Y30WAH}$ were present as intact holotoxins (Table 2).

TABLE 2

Native Gel Assay for Intact Holotoxin

| CT-CRM | % of holotoxin |
|---|---|
| CT-CRM$_{R25W}$ | >95 |
| CT-CRM$_{R25G}$ | 91.0 |
| CT-CRM$_{T48TH}$ | 91.20 |
| CT-CRM$_{G34GGP}$ | 98.80 |
| CT-CRM$_{Y30WAH}$ | 90.93 |

EXAMPLE 3

Y-1 Adrenal Cell Assay for Residual Toxicity of CT-CRMs

Mutant CT-CRMs were compared with wild-type CT for toxicity in the mouse Y-1 adrenal tumor cell assay, which is used in vitro to measure toxicity of enterotoxins in the cholera toxin/heat labile enterotoxin family. The assay depends upon binding of the toxin to cell surface receptors, and the subsequent entry of the A1 subunit of the toxin into the cytoplasm of the cell.

Native cholera toxin isolated from *V. cholerae* is proteolytically nicked at the A1-A2 junction, resulting in the A1 and A2 subunits being held together by only a disulfide bond. This makes the A1 and A2 subunits unstable and easily dissociable from each other. The A1 subunit of the nicked CT dissociates from the A2 subunit upon binding to the cell surface receptor, and enters the cell, where it ADP-ribosylates the regulatory G-protein (Gsα), leading to its toxic effects as described above. In contrast, enterotoxin produced in *E. coli* (either CT or LT) is unnicked, and thus, has the A1-A2 peptides still joined. Consequently, the CT produced in *V. cholerae* is significantly more toxic in the Y-1 adrenal cell assays than the CT produced in a heterologous bacterial cell such as *E. coli*.

In a first Y-1 adrenal cell assay, mutant CT-CRMs were compared to nicked wild-type CT from *V. cholerae* for toxicity. In this assay, Y-1 adrenal cells (ATCC CCL-79) were seeded in 96-well flat-bottom plates at a concentration of $10^4$ cells per well. Thereafter, three-fold serial dilutions of purified (~90% purity as determined by Coomassie staining) CT-CRMs were added to the tumor cells and incubated at 37° C. (5% CO$_2$) for 18 hours. The cells were then examined by light microscopy for evidence of toxicity (cell rounding). The endpoint titer was defined as the minimum concentration of toxin required to give greater than 50% cell rounding. The percent of residual toxicity was then calculated using the endpoint titer of wild-type nicked CT from *V. cholera* (100% toxicity) divided by the titer elicited by CT-CRMs multiplied by 100. The data set forth in Table 3 indicate that the residual toxicity of the five purified mutant holotoxins, CT-CRM$_{R25W}$, CT-CRM$_{R25G}$, CT-CRM$_{T48TH}$, CT-CRM$_{G34GGP}$ and CT-CRM$_{Y30WAH}$ tested using the Y-1 adrenal cell assay was substantially reduced.

TABLE 3

Y-1 Adrenal Cell Assay

| CT-CRM | % Residual Toxicity |
|---|---|
| CT-CRM$_{R25W}$ | 0.37 |
| CT-CRM$_{R25G}$ | 0.041 |
| CT-CRM$_{T48TH}$ | 0.12 |
| CT-CRM$_{G34GGP}$ | 1.11 |
| CT-CRM$_{Y30WAH}$ | 0.12 |

In a second independent study, crude periplasmic extracts of *E. coli* cells (TG1) expressing elevated levels of mutant CT-CRMs, were compared against unnicked wild-type CT holotoxin expressed in *E. coli* for residual toxicity in Y-1 adrenal cell assay. Y-1 adrenal cells were incubated in multi-well dishes in an RPMI medium containing 10% fetal calf serum in the presence of crude *E. coli* cell lysate. Cell toxicity was monitored as before. In this study, one toxic unit was defined as the smallest amount of toxin or supernatant that caused rounding of 75-100% of the cells in a well after overnight incubation. The results of this study are presented in Table 4 below.

TABLE 4

Y-1 Adrenal Cell Assay

| CT-CRM | % Residual Toxicity |
|---|---|
| CT-CRM$_{R25W}$ | 30 |
| CT-CRM$_{R25G}$ | 6 |
| CT-CRM$_{T48TH}$ | 25 |
| CT-CRM$_{G34GGP}$ | 30 |
| CT-CRM$_{Y30WAH}$ | 8 |

The results of this study indicated that while the toxicities of CT-CRM$_{R25G}$ and CT-CRM$_{Y30WAH}$ were substantially reduced, the toxicities of CT-CRM$_{R25W}$ and CT-CRM$_{T48TH}$ were approximately 30% of the toxicity of wild-type CT. Without being bound by theory, the variant results in the second study (Table 4) may be attributable to the fact that periplasmic crude *E. coli* cell lysates used in the second study contained unnicked mutant CT-CRMs. Another contributing factor may be that toxicity was measured as a percentage of the toxicity of wild-type, unnicked CT produced by *E. coli*, wherein the unnicked wild-type CT from *E. coli* had a 50% cell rounding dose of 6250 pg/ml in the same Y1 cell assay (data not shown). In contrast, in the first study, the residual cytotoxicity of the mutant CT-CRMs is expressed as a percentage of the toxicity of wild-type, nicked CT produced by *V. cholerae*, wherein the nicked holotoxin had a 50% cell rounding dose of 125 pg/ml in the same Y1 cell assay. Consequently, the residual toxicity reported in the second study is 50 fold higher than that obtained in the first study.

EXAMPLE 4

The ADP-Ribosyltransferase Assay

NAD$^+$:agmatine ADP-ribosyltransferase activity was measured as the release of [carbonyl-$^{14}$C] nicotinamide from radiolabeled NAD$^+$. Briefly, CT and CT-CRMs were trypsin activated and incubated for 30 minutes at 30° C. with 50 mM glycine/20 mM dithiothreitol in TEAN buffer (Tris/EDTA/ sodium azide/sodium chloride) (pH 8.0). Thereafter, the following materials were added to the reaction: 0.1 µg of soybean trypsin inhibitor, 50 mM potassium phosphate, 10 mM agmatine, 20 mM dithiothreitol, 10 mM magnesium chloride, 100 µM GTP, 3 mM dimyristoylphosphatidylcholine, 0.2% cholate, 0.03 mg of ovalbumin, 100 µM [adenine-U-$^{14}$C]NAD (DuPont NEN™, Boston, Mass.) and water to a final volume of 300 µl. After incubation for 90 minutes at 30° C., 100 µl samples were applied to columns (0.64×5 cm) of AG1-X2 (Bio-Rad), which were washed five times with 1.0 ml of distilled/deionized H$_2$O. Eluates containing [$^{14}$C]ADP-ribosylagmatine were collected for radioassay. Mean recovery of $^{14}$C in the eluate is expressed as percentage of that applied to column. The results are presented in Table 5.

TABLE 5

NAD:Agmatine ADP-Ribosyltransferase Activity

| CT/CT-CRM | ADP-ribosylagmatine formed (nmol/hr/µg protein) | % ADP-ribosylation activity |
|---|---|---|
| CT, 10 µg | 35.7 | 100 |
| CT-CRM$_{R25W}$ | 1.6 | 4.5 |
| CT-CRM$_{R25G}$ | 1.0 | 2.7 |
| CT-CRM$_{T48TH}$ | 1.2 | 3.4 |
| CT-CRM$_{G34GGP}$ | 1.8 | 5.0 |
| CT-CRM$_{Y30WAH}$ | 1.6 | 4.5 |

ADP-ribosyltransferase activity was also independently determined using diethylamino (benzylidine-amino) guanidine (DEABAG) as a substrate (Jobling, MG and Holmes, R K 2001 *J. Bacteriol.*, 183(13):4024-32). In this assay, 25 μl aliquots of mutant CT-CRMs from purified cell lysates, activated for 30 minutes at 30° C. with 1/50 w/w trypsin, were incubated with 200 μl 2 mM DEABAG in 0.1M $K_2PO_4$, pH 7.5, 10 μM NAD, 4 mM DTT for two hours. The reaction was stopped by adding 800 μl of a slurry buffer containing 400 mg DOWEX AG50-X8 resin to bind unreacted substrate. ADP-ribosylated DEABAG in the supernatant was quantitated by florescence emission in a DyNA Quant fluorimeter calibrated with DEABAG. With the exception of the mutants CT-CRM$_{G34GGP}$ and CT-CRM$_{Y30WAH}$, the ADP ribosyl-transferase activities of the mutant CT-CRMs were substantially reduced over that of wild-type (Table 6). The high level of ADP-ribosyl-transferase activity seen with CT-CRM$_{G34GGP}$ and CT-CRM$_{Y30WAH}$ may be attributable to the fact that in this study the ADP ribosyl-transferase activity of mutant CT-CRMs was measured using a different substrate in a different assay protocol.

TABLE 6

ADP-ribosyltransferase Activity of CT-CRMs using Diethylamino (benzylidine-amino) Guanidine (DEABAG)

| CT/CT-CRM | % ADP-ribosylation Activity |
|---|---|
| CT | 100 |
| CT-CRM$_{R25W}$ | 10 |
| CT-CRM$_{R25G}$ | 0.5 |
| CT-CRM$_{T48TH}$ | 18 |
| CT-CRM$_{G34GGP}$ | 54 |
| CT-CRM$_{Y30WAH}$ | 43 |

EXAMPLE 5

Immune Responses of BALB/C Mice Immunized with Recombinant P4 Outer Membrane Protein (rP4) of Nontypable *Haemophilus influenzae* (NTHi) Alone or in Conjunction with CT-CRMS BALB/c mice (6-8 weeks old, 5 mice/group) were immunized at weeks 0, 3 and 5 with recombinant P4 protein (rP4, 5 μg per dose) in saline or co-formulated with wild-type CT, CT-CRM$_{E29H}$, CT-CRM$_{T48TH}$, CT-CRM$_{G34GGP}$, CT-CRM$_{Y30WAH}$, CT-CRM$_{R25W}$ or CT-CRM$_{R25G}$ at a dose 1.0 μg per immunization. A total volume of 10 μl was administered intranasally (5 μl per nostril). Mice were bled at weeks 0, 2, 3, 4, 5 or 6 in order to assay serum antibody responses. One week after the last immunization (week 6), mice were sacrificed for the analysis of mucosal antibody responses.

Significant differences between groups were determined by the Tukey-Kramer HSD multiple comparisons test (for rP4 protein) or by the Student t-test (for UspA2) using JMP® statistical discovery software (SAS Institute Inc., Cary, N.C.).

Analysis of serum antibodies at weeks 0, 3, 5 and 6 showed that immunization with NTHi rP4 protein formulated with any of the CT-CRM mutants, disclosed herein at a concentration of 1 μg/dose, significantly induced immune responses to rP4 protein. The magnitude of the total IgG immune response to rP4 protein was increased approximately 15-35 fold by inclusion of the CT-CRM mutants in the formulation. No significant differences were observed in total anti-rP4 IgG titers among the new mutant toxins (CT-CRM$_{T48TH}$, CT-CRM$_{G34GGP}$, CT-CRM$_{Y30WAH}$, CT-CRM$_{R25W}$ and CT-CRM$_{R25G}$) even though they all elicited significantly higher IgG titers than rP4 protein alone by Student t-test (Table 6). Individual serum analysis of IgA antibodies showed that only formulation rP4/CT-CRM$_{R25G}$ elicited significantly higher titers of IgA antibodies to rP4 protein than the control group receiving rP4 protein in saline (Table 7). The use of each of the new CT-CRM mutants also enhanced serum IgG subclass antibodies (IgG1, IgG2a and IgG2b) to rP4 protein (Table 9).

Anti-rP4 protein antibody responses were also analyzed in pooled mucosal wash samples (Table 8). As expected, no induction of antibody in BAL and NW from rP4/saline immunized mice was observed. However, the potent mucosal adjuvant capacity of CT-CRM$_{T48TH}$, CT-CRM$_{Y30WAH}$ and CT-CRM$_{R25G}$ was clearly demonstrable. Although no statistical analysis can be performed on these pooled samples, some trends appeared. For example, mice that received CT-CRM$_{T48TH}$, CT-CRM$_{Y30WAH}$ and CT-CRM$_{R25G}$ displayed elevated rP4 specific IgA antibodies in each of the saliva, NW and VW samples tested.

Additionally, anti-CT antibody responses were also determined. As shown in Tables 7-11, all the CT mutants enhanced the systemic and mucosal CT-specific antibody responses one-week after the last immunization. However, it should be noted that the mice in the above study were, subsequent to the completion of the study, determined to be infected with the mouse hepatitis virus.

TABLE 7

The Effect of Mutant Cholera Toxins on the Immunogenicity of
NTHi LrP4 Protein following Intranasal Immunization in BALB/c Mice.
Anti-rLP4 Antibody Titers[c] (Pooled Sera)[d]

| | | | Week 0 | | Week 3 | | Week 5 | | Week 6 | |
|---|---|---|---|---|---|---|---|---|---|---|
| Immunogen | Rte[a] | Adjuvant[b] | IGA[b] | IgG | IgA | IgG | IgA | IgG | IgA | IgG |
| NTHi LrP4 | IN | — | <100 | <100 | <100 | 168 | <100 | 532 | 122 | 3,638 |
| NTHi LrP4 | IN | CT | | | <100 | 120 | <100 | 795 | 198 | 18,584 |
| NTHi LrP4 | IN | CT-CRM$_{E29H}$ | | | <100 | <100 | <100 | 576 | 152 | 4,854 |
| NTHi LrP4 | IN | CT-CRM$_{T48TH}$ | | | <100 | 102 | 111 | 10,594 | 453 | 55,775 |
| NTHi LrP4 | IN | CT-CRM$_{G34GGP}$ | | | <100 | 146 | 196 | 1,701 | 434 | 68.325 |
| NTHi LrP4 | IN | CT-CRM$_{Y30WAH}$ | | | <100 | <100 | <100 | 3,406 | 391 | 93,502 |
| NTHi LrP4 | IN | CT-CRM$_{R25W}$ | | | <100 | 187 | 116 | 16,809 | 509 | 127,130 |
| NTHi LrP4 | IN | CT-CRM$_{R25G}$ | | | <100 | 278 | 273 | 23,163 | 1,056 | 62,323 |

[a]Female BALB/c mice were immunized with NTHi rP4 (5 µg) at weeks 0, 3, and 5. IN vax = 10 µl
[b]NTHi rP4 immunogens were formulated with saline or 1 µg each of Cholera Toxin, CT-CRM$_{E29H}$, CT-CRM$_{T48TH}$, CT-CRM$_{G34GGP}$, CT-CRM$_{Y30WAH}$, CT-CRM$_{R25W}$, or CT-CRM$_{R25G}$
[c]ELISAs were performed using 0.2 µg NTHI rP4 per well and with an endpoint titer determination of 0.1 at OD$_{405}$.
[d]Sera samples were collected at weeks 0, 3, 5 and 6; pooled samples represent an n of 5.

TABLE 8

The Effect of Mutant Cholera Toxins on the Immunogenicity of
NTHi LrP4 Protein following Intranasal Immunization in BALB/c Mice.
Anti-rLP4 Antibody Titers[c] (Pooled Mucosal Washes)[d]

| | | | SAL | | BAL | | VW | | NW | |
|---|---|---|---|---|---|---|---|---|---|---|
| Immunogen | Rte[a] | Adjuvant[b] | IgA | IgG | IgA | IgG | IgA | IgG | IgA | IgG |
| NTHi LrP4 | IN | — | 19 | <10 | <10 | <10 | 33 | <10 | <10 | <10 |
| NTHi LrP4 | IN | CT | <10 | <10 | <10 | 23 | <10 | <10 | <10 | <10 |
| NTHi LrP4 | IN | CT-CRM$_{E29H}$ | <10 | <10 | <10 | <10 | 33 | <10 | <10 | <10 |
| NTHi LrP4 | IN | CT-CRM$_{T48TH}$ | 105 | <10 | <10 | 79 | 73 | 21 | 12 | <10 |
| NTHi LrP4 | IN | CT-CRM$_{G34GGP}$ | 17 | <10 | <10 | 80 | 11 | 23 | <10 | 13 |
| NTHi LrP4 | IN | CT-CRM$_{Y30WAH}$ | 25 | <10 | <10 | 113 | 48 | 47 | 10 | 19 |
| NTHi LrP4 | IN | CT-CRM$_{R25W}$ | 37 | <10 | <10 | 169 | 20 | 23 | <10 | <10 |
| NTHi LrP4 | IN | CT-CRM$_{R25G}$ | 185 | <10 | <10 | 64 | 348 | 32 | 23 | <10 |

[a]Female BALB/c mice were immunized with NTHi rP4 (5 µg) at weeks 0, 3, and 5. IN vax = 10 µl
[b]NTHi rP4 immunogens were formulated with saline or 1 µg each of Cholera Toxin, CT-CRM$_{E29H}$, CT-CRM$_{T48TH}$, CT-CRM$_{G34GGP}$, CT-CRM$_{Y30WAH}$, CT-CRM$_{R25W}$, or CT-CRM$_{R25G}$
[c]ELISAs were performed using 0.2 µg NTHI rP4 per well and with an endpoint titer determination of 0.1 at OD$_{405}$.
[d]Mucosal samples were collected at week 6, day 1; pooled samples represent an n of 5.

TABLE 9

The Effect of Mutant Cholera Toxins on the Immunogenicity of
NTHi LrP4 Protein following Intranasal Immunization in BALB/c Mice.
Anti-rLP4 Antibody Titers[c] (Week 6 Pooled Sera)[d]

| Immunogen | Rte[a] | Adjuvant[b] | IgG1 | IgG2a | IgG2b | IgG3 |
|---|---|---|---|---|---|---|
| NTHi LrP4 | IN | — | 1,165 | 1,891 | 1,245 | <100 |
| NTHi LrP4 | IN | CT | 625 | 14,989 | 9,284 | 278 |
| NTHi LrP4 | IN | CT-CRM$_{E29H}$ | 1,630 | 2,618 | 845 | <100 |
| NTHi LrP4 | IN | CT-CRM$_{T48TH}$ | 11,220 | 35,239 | 20,733 | 206 |
| NTHi LrP4 | IN | CT-CRM$_{G34GGP}$ | 12,583 | 48,134 | 24,267 | <100 |
| NTHi LrP4 | IN | CT-CRM$_{Y30WAH}$ | 13,894 | 59,049 | 28,975 | 744 |
| NTHi LrP4 | IN | CT-CRM$_{R25W}$ | 24,373 | 89,892 | 37,389 | 422 |
| NTHi LrP4 | IN | CT-CRM$_{R25G}$ | 7,957 | 46,776 | 16,731 | 256 |

[a]Female BALB/c mice were immunized with NTHi rP4 (5 µg) at weeks 0, 3, and 5. IN vax = 10 µl
[b]NTHi rP4 immunogens were formulated with saline or 1 µg each of Cholera Toxin, CT-CRM$_{E29H}$, CT-CRM$_{T48TH}$, CT-CRM$_{G34GGP}$, CT-CRM$_{Y30WAH}$, CT-CRM$_{R25W}$, or CT-CRM$_{R25G}$
[c]ELISAs were performed using 0.2 µg NTHI rP4 per well and with an endpoint titer determination of 0.1 at OD$_{405}$.
[d]Sera samples were collected at weeks 0, 3, 5 and 6; pooled samples represent an n of 5.

TABLE 10

The Effect of Mutant Cholera Toxins on the Immunogenicity of
NTHi LrP4 Protein following Intranasal Immunization in BALB/c Mice.
Anti-rLP4 Antibody Titers on Individual Sera[c,d]

| Immunogen | Rte[a] | Adjuvant[b] | 1 | 2 | 3 | 4 | 5 | GeoMean[e] | StDev |
|---|---|---|---|---|---|---|---|---|---|
| NTHi LrP4 | IN | — | 35 | 114 | 61 | 79 | 316 | 121 | 113 |
| NTHi LrP4 | IN | CT | 139 | 48 | 145 | 85 | 461 | 176 | 165 |
| NTHi LrP4 | IN | CT-CRM$_{E29H}$ | 33 | 126 | 333 | 26 | 49 | 113^ | 129 |
| NTHi LrP4 | IN | CT-CRM$_{T48TH}$ | 468 | 780 | 530 | 76 | 218 | 414 | 275 |
| NTHi LrP4 | IN | CT-CRM$_{G34GGP}$ | 177 | 479 | 963 | 175 | 214 | 402 | 338 |
| NTHi LrP4 | IN | CT-CRM$_{Y30WAH}$ | 271 | 443 | 408 | 699 | 282 | 421 | 173 |
| NTHi LrP4 | IN | CT-CRM$_{R25W}$ | 431 | 198 | 361 | 360 | 835 | 437 | 238 |
| NTHi LrP4 | IN | CT-CRM$_{R25G}$ | 1,037 | 462 | 1,851 | 1,825 | 678 | 1,171*^ | 643 |

[a]Female BALB/c mice were immunized with NTHi rP4 (5 µg) at weeks 0, 3, and 5. IN vax = 10 µl
[b]NTHi rP4 immunogens were formulated with saline or 1 µg each of Cholera Toxin, CT-CRM$_{E29H}$, CT-CRM$_{T48TH}$, CT-CRM$_{G34GGP}$, CT-CRM$_{Y30WAH}$, CT-CRM$_{R25W}$, or CT-CRM$_{R25G}$
[c]ELISAs were performed using 0.2 µg NTHI rP4 per well and with an endpoint titer determination of 0.1 at OD$_{405}$.
[d]Sera samples were collected at weeks 0, 3, 5 and 6; pooled samples represent an n of 5.
[e]*denotes significant difference compared to saline control; ^denotes significant difference compared to other IN groups.

TABLE 11

The Effect of Mutant Cholera Toxins on the Immunogenicity of
NTHi LrP4 Protein following Intranasal Immunization in BALB/c Mice.
Anti-rLP4 Antibody Titers on Individual Sera[c,d]

| Immunogen | Rte[a] | Adjuvant[b] | 1 | 2 | 3 | 4 | 5 | GeoMean[e] | StDev |
|---|---|---|---|---|---|---|---|---|---|
| NTHi LrP4 | IN | — | 112 | 2,393 | 2,885 | 4,432 | 8,471 | 3,659 | 3,104 |
| NTHi LrP4 | IN | CT | 22,042 | 5,499 | 13,292 | 10,746 | 24,920 | 15,300 | 8,044 |
| NTHi LrP4 | IN | CT-CRM$_{E29H}$ | 3,063 | 16,889 | 179 | 204 | 1,406 | 4,348^ | 7,109 |
| NTHi LrP4 | IN | CT-CRM$_{T48TH}$ | 63,090 | 52,393 | 53,912 | 13,017 | 38,604 | 44,203* | 19,506 |
| NTHi LrP4 | IN | CT-CRM$_{G34GGP}$ | 63,924 | 63,908 | 73,793 | 59,169 | 50,229 | 62,205* | 8,555 |
| NTHi LrP4 | IN | CT-CRM$_{Y30WAH}$ | 63,522 | 65,791 | 31,934 | 174,833 | 130,173 | 93,251* | 57,915 |
| NTHi LrP4 | IN | CT-CRM$_{R25W}$ | 138,982 | 88,085 | 160,963 | 74,885 | 151,979 | 122,979* | 38,957 |
| NTHi LrP4 | IN | CT-CRM$_{R25G}$ | 47,114 | 15,915 | 154,578 | 34,780 | 17,598 | 54,003* | 57,680 |

[a]Female BALB/c mice were immunized with NTHi rP4 (5 µg) at weeks 0, 3, and 5. IN vax = 10 µl
[b]NTHi rP4 immunogens were formulated with saline or 1 µg each of Cholera Toxin, CT-CRM$_{E29H}$, CT-CRM$_{T48TH}$, CT-CRM$_{G34GGP}$, CT-CRM$_{Y30WAH}$, CT-CRM$_{R25W}$, or CT-CRM$_{R25G}$
[c]ELISAs were performed using 0.2 µg NTHI rP4 per well and with an endpoint titer determination of 0.1 at OD$_{405}$.
[d]Sera samples were collected at weeks 0, 3, 5 and 6; pooled samples represent an n of 5.
[e]*denotes significant difference compared to saline control; ^denotes significant difference compared to other IN groups.

EXAMPLE 6

The Immune Responses of BALB/C Mice Immunized with the UspA2 Outer Membrane Protein of *M. Catarrhalis*

In this study, the capacity of mutant CT-CRMs to augment systemic and mucosal immune responses against the native UspA2 outer membrane protein of *M. catarrhalis* was examined. BALB/C mice (6-8 weeks old, 5 mice/group) were immunized at weeks 0, 3, and 5. Purified UspA2 (5 µg/dose) alone in 10 µl saline or in a 10 µl formulation containing 0.1 µg/dose of wild-type CT or a mutant CT-CRM (CT-CRM$_{E29H}$, CT-CRM$_{R25W}$, CT-CRM$_{R25G}$, CT-CRM$_{T48TH}$, CT-CRM$_{G34GGP}$, or CT-CRM$_{Y30WAH}$) was administered to Balb/C mice IN (5 ul/nostril) on week 0, 2 and 4. Analysis of serum antibodies at weeks 0, 2, 4 and 6 showed that immunization with UspA2 formulated with any of the aforementioned CT-CRM mutants except CT-CRM$_{R25G}$, at a concentration of 0.1 µg/dose, enhanced antibody responses to UspA2 (Table 12). The magnitude of the total IgG immune response to UspA2 was increased approximately 3-10 fold by inclusion of the CT-derived mutants. CT-CRM$_{G34GGP}$, CT-CRM$_{E29H}$ or wild-type CT elicited significantly higher IgG titers than UspA2/PBS by Student t-test. However, no significant differences were observed in total anti-UspA2 IgG titers between each of the new mutant toxins (CT-CRM$_{E29H}$, CT-CRM$_{T48TH}$, CT-CRM$_{G34GGP}$, CT-CRM$_{Y30WAH}$, CT-CRM$_{R25W}$, or CT-CRM$_{R25G}$). The use of each of the CT mutants except CT-CRM$_{R25W}$, also enhanced serum IgG1, IgG2a and IgG2b antibodies to UspA2 (Table 12).

Anti-UspA2 antibody responses were also analyzed in pooled mucosal wash samples (Table 13). As expected, no induction of antibody in mucosal washes from UspA2/PBS immunized mice was observed. However, the potent mucosal adjuvant capacity of each mutant CT was clearly demonstrated. Although no statistical analyses were performed on these pooled samples, some trends emerged. For example, mice that received CT-CRM$_{G34GGP}$ displayed elevated IgG or IgA titers to UspA2 in each of the bronchoalveolar lavage (BAL), nasal wash (NW) and vaginal wash (VW) samples collected (Table 13). In comparison, none of the new mutant toxins appeared to be better than CT-CRM$_{E29H}$ or wild-type CT in adjuvanting local immune responses to UspA2 protein. Protein-specific IgG and IgA levels in the serum and in mucosal lavages were also examined on day 28. All mutant CTs elicited enhanced serum IgG antibody response (data not shown). The levels of IgG and IgA in bronchial, nasal and vaginal washes were also measured. No IgA was detected in any of the washes, and IgG was detected only in a few washes (Table 13). The mice in this study were, subsequent to the completion of the study, determined to be infected with the mouse hepatitis virus.

TABLE 12

Sera IgG subclass titers against UspA2 Week 6 *

| Antigen | Adjuvant | IgG1 | IgG2a | IgG2b | IgG3 | IgG1/G2a Ratio |
|---|---|---|---|---|---|---|
| UspA2 | None | 600 | 346 | 320 | <100 | 1.7 |
| UspA2 | CT-CRM$_{E29H}$ | 3,443 | 6,655 | 4,027 | <100 | 0.52 |
| UspA2 | CT-CRM$_{T48TH}$ | 1,350 | 809 | 429 | <100 | 1.6 |
| UspA2 | CT-CRM$_{G34GGP}$ | 5,918 | 4,480 | 3,111 | <100 | 1.32 |
| UspA2 | CT-CRM$_{Y30WAH}$ | 1,991 | 1,618 | 809 | <100 | 1.23 |
| UspA2 | CT-CRM$_{R25W}$ | 1,772 | 1,100 | 1,095 | <100 | 1.61 |
| UspA2 | CT-CRM$_{R25G}$ | 301 | 221 | 224 | <100 | 1.36 |
| UspA2 | CT | 9,050 | 18,227 | 10,195 | 189 | 0.5 |

* BALB/c mice (5/group) were immunized intranasally at weeks 0, 2, 4. Sera and mucosal washes collected at week 6. The antigen dose was 5 µg, and adjuvant dose was 0.1 µg per animal. IgG subclass determined by ELISA on pooled sera.

TABLE 13

Mucosal IgG & IgA titers against UspA2 *

| | | BW | | NW | | VW | |
|---|---|---|---|---|---|---|---|
| Antigen | Adjuvant | IgG | IgA | IgG | IgA | IgG | IgA |
| UspA2 | None | <10 | <10 | <10 | <10 | <10 | <10 |
| UspA2 | CT-CRM$_{E29H}$ | 16 | <10 | <10 | 20 | 24 | 506 |
| UspA2 | CT-CRM$_{T48TH}$ | <10 | <10 | <10 | <10 | <10 | 58 |
| UspA2 | CT-CRM$_{G34GGP}$ | 17 | <10 | <10 | 31 | 24 | 285 |
| UspA2 | CT-CRM$_{Y30WAH}$ | <10 | <10 | <10 | 32 | <10 | 208 |
| UspA2 | CT-CRM$_{R25W}$ | <10 | <10 | <10 | 20 | <10 | 29 |
| UspA2 | CT-CRM$_{R25G}$ | <10 | <10 | <10 | <10 | <10 | <10 |
| UspA2 | CT | 40 | <10 | <10 | 85 | 111 | 774 |

* BALB/c mice (5/group) were immunized intranasally at weeks 0, 2, 4. Sera and mucosal washes collected at week 6. The antigen dose was 5 µg, and adjuvant dose was 0.1 µg per animal. IgG and IgA titers determined by ELISA on pooled sera

EXAMPLE 7

Adjuvanticity of the Mutant Cholera Toxin Holotoxins

To create a comprehensive panel of mutant CT-CRMs with different characteristics of toxicity, functionality and immunogenicity, the above-described CT-CRM mutants were analyzed as mucosal adjuvants, and the toxicity and enzymatic activity profiles of each of the mutants were determined. As summarized in Tables 14 through 18, all mutant CT-CRMs have significantly reduced toxicity and enzyme activity compared to wild-type CT. These genetically detoxified mutant CTs were evaluated for their capacity to adjuvant immune responses to native UspA2 protein from *M. catarrhalis*.

The experiments were performed as follows: BALB/c mice (6-8 weeks old, 5 mice/group) were immunized at weeks 0, 2 and 4 with 5 µg of purified native UspA2 protein in PBS or co-formulated with doses of 0.1 or 1.0 µg per immunization of wild-type CT, or CT-CRM$_{E29H}$, or CT-CRM$_{T48TH}$, or CT-CRM$_{G34GGP}$, or CT-CRM$_{Y30WAH}$, or CT-CRM$_{R24W}$ or CT-CRM$_{R25G}$. A total volume of 10 µl was administered intranasally (5 µl per nostril). Mice were bled at weeks 0, 2, 4, or 6 in order to assay serum antibody responses. Two weeks after the last immunization (week 6), mice were sacrificed for the analysis of mucosal antibody responses. UspA2 ELISA titers were determined at an endpoint of 0.1 at OD$_{405}$. Significant differences between groups were determined by the Tukey-Kramer HSD multiple comparisons test using JMP® statistical discovery software (SAS Institute Inc., Cary, N.C.).

Adjuvanticity of the CT-CRMs can be summarized as follows. Analysis of serum IgG and IgA antibodies at weeks 2, 4 and 6 showed that immunization with UspA2 protein formulated with any of the CT-CRM mutants, except CT-CRM$_{R25G}$, at a concentration of 1 µg/dose, significantly enhanced antibody responses to UspA2 protein (Table 15). The magnitude of the total IgG immune response to UspA2 protein was increased approximately 11-68 fold by inclusion of the CT-derived mutants (excluding CT-CRM$_{R25G}$) (Table 16). CT-CRM$_{T48TH}$, CT-CRM$_{Y30WAH}$, CT-CRM$_{R25W}$ (at 1 µg dose), and CT-CRM$_{G34GGP}$ (at both 0.1 µg and 1 µg doses) elicited significantly higher IgG and IgA titers than UspA2/PBS by Tukey-Kramer analysis. However, no significant differences were observed in total anti-UspA2 IgG titers between each of the new mutant toxins excluding CT-CRM$_{R25G}$ (Table 16). The use of each of the CT mutants except CT-CRM$_{R25G}$ at a 1 µg dose also enhanced serum IgG1, IgG2a and IgG2b antibodies to UspA2 (Table 17). The ratio of the IgG1 and IgG2a/IgG2b titers was approximately 1.0, indicating a balanced Th1/Th2 type of immune response.

Anti-UspA2 protein antibody responses were also analyzed in pooled mucosal wash samples (Table 18). As expected, no induction of antibody in mucosal washes from UspA2/PBS immunized mice was observed. However, the potent mucosal adjuvant capacity of each mutant CT-CRM, excluding CT-CRM$_{R25G}$ was clearly demonstrated. There were UspA2 specific mucosal IgA antibodies detected in most of the mucosal samples. Although no statistical analysis can be performed on these pooled samples, some trends appeared. For example, mice that received CT-CRM$_{G34GGP}$ or CT-CRM$_{R25W}$ displayed elevated IgG or IgA antibodies to UspA2 protein in each of the bronchoalveolar lavage, the nasal wash and the vaginal wash samples collected, similar to the wild-type CT or CT-CRM$_{E29H}$.

These CT-CRMs, except CT-CRM$_{R25G}$, are potent mucosal adjuvants for *M. catarrhalis* UspA2 protein. The serum antibody data showed that all the CT-CRMs except CT-CRM$_{R25G}$ at 1 µg dose are equally as capable in adjuvanting immune responses to UspA2 protein as is CT-CRM$_{E29H}$ (Table 16). At 0.1 µg of dose, CT-CRM$_{G34GGP}$ appeared to be more potent than CT-CRM$_{E29H}$ at the same dose (Table 16). The mucosal wash data appears to suggest that all of these mutant CT-CRMs except CT-CRM$_{R25G}$, retain potent mucosal adjuvant properties (Table 18). Furthermore, they all have significantly lower residual toxicity and enzyme activity than wild-type CT as shown in Table 14. Therefore, these mutant CT-CRMs are additional effective mucosal adjuvants.

TABLE 14

Characterization of the Mutant Cholera Toxins

| Mutant CT | Homogeneity (%) | Holotoxin (%) | Y-1 cell toxicity (%) | ADP-Ribosyl-transferase activity (%) |
|---|---|---|---|---|
| CT-CRM$_{T48TH}$ | 100.0 | 91.0 | 0.12 | 3.4 |
| CT-CRM$_{G34GGP}$ | 100.0 | 98.8 | 1.11 | 5.0 |
| CT-CRM$_{Y30WAH}$ | 99.0 | 90.9 | 0.12 | 4.5 |
| CT-CRM$_{R25W}$ | 100.0 | >95.0 | 0.37 | 4.5 |
| CT-CRM$_{R25G}$ | 99.7 | 91.2 | 0.041 | 2.7 |

TABLE 15

Adjuvant Effects of Mutant CT on the Immune Response to UspA2 Delivered IN to Female BALB/c Mice

| Antigen (5 µg) | Adjuvant | Dose | week 2 IgG | week 2 IgA | week 4 IgG | week 4 IgA | week 6 IgG | week 6 IgA |
|---|---|---|---|---|---|---|---|---|
| UspA2 | None | PBS | <100 | <100 | <100 | <100 | <500 | <50 |
| UspA2 | CT-CRM$_{E29H}$ | 1 µg | 182 | 54 | 3,777 | <100 | 11,305 | 194 |
|  |  | 0.1 µg | <100 | <100 | 160 | <100 | 544 | <50 |
| UspA2 | CT-CRM$_{T48TH}$ | 1 µg | <100 | <100 | 967 | <100 | 3,542 | 128 |
|  |  | 0.1 µg | <100 | <100 | <100 | <100 | 568 | <50 |
| UspA2 | CT-CRM$_{G34GGP}$ | 1 µg | 298 | <100 | 6,170 | 83 | 15,498 | 398 |
|  |  | 0.1 µg | 125 | <100 | 775 | <100 | 2,900 | 98 |
| UspA2 | CT-CRM$_{Y30WAH}$ | 1 µg | 206 | <100 | 1,275 | <100 | 3,330 | 81 |
|  |  | 0.1 µg | <100 | <100 | <100 | <100 | <500 | <50 |
| UspA2 | CT-CRM$_{R25W}$ | 1 µg | 304 | <100 | 8,335 | <100 | 16,308 | 196 |
|  |  | 0.1 µg | <100 | <100 | 214 | <100 | 989 | <50 |
| UspA2 | CT-CRM$_{R25G}$ | 1 µg | <100 | <100 | 232 | <100 | <1,000 | <50 |
|  |  | 0.1 µg | <100 | <100 | <100 | <100 | <500 | <50 |
| UspA2 | Cholera Toxin | 1 µg | 191 | <100 | 6,119 | <100 | 13,588 | 254 |
|  |  | 0.1 µg | 351 | <100 | 5,472 | 108 | 20,632 | 399 |

BALB/c mice (groups of 5) were immunized IN with a 10 ul volume at weeks 0, 2, & 4. Sera were collected at week 6. The UspA2 ELISA titers were determined at an endpoint of 0.1 at OD$_{405}$. The Tukey-Kramer analysis showed the following: The 1 µg dose of each adjuvant is statistically significant from the same adjuvant at 0.1 g dose, except the IgG of CT, CT-CRM$_{G34GGP}$ and IgA of CT-CRM$_{R25G}$. Results in Table 16 reported with an asterisk (*) are statistically significant from the UspA2/PBS group. Results indicated with footnote a ($^a$) are statistically significantly higher than all 0.1 µg doses (except CT) and the 1 µg dose of CT-CRM$_{R25G}$. Results indicated with footnote b ($^b$) are statistically significantly lower than all 1 µg doses except the 1 µg dose of CT-CRM$_{T48TH}$. Results indicated with footnote c ($^c$) are statistically significantly higher than all 0.1 µg doses (except CT) and the 1 µg dose of CT-CRM$_{R25G}$. Results indicated with a footnote d ($^d$) are statistically significantly lower than all 1 µg doses and also the 0.1 µg dose of CT and CT-CRM$_{G34GGP}$.

TABLE 16

Individual Serum Analysis of IgG and IgA Titers against UspA2

| Antigen (5 µg) | Adjuvant | Dose | Serum Anti-UspA2 Protein Antibody Titers (Mean Log$_{10}$) IgG | IgA |
|---|---|---|---|---|
| UspA2 | PBS | — | 2.21 ± 0.36 | <25 |
| UspA2 | CT-CRM$_{E29H}$ | 1 µg | 4.33 ± 0.19* | 2.59 ± 0.20* |
|  |  | 0.1 µg | 2.68 ± 0.34 | 1.16 ± 0.13 |
| UspA2 | CT-CRM$_{T48TH}$ | 1 µg | 3.74 ± 0.45* | 2.20 ± 0.66* |
|  |  | 0.1 µg | 2.51 ± 0.56 | <25 |
| UspA2 | CT-CRM$_{G34GGP}$ | 1 µg | 4.53 ± 0.11* | 2.76 ± 0.15* |
|  |  | 0.1 µg | 3.95 ± 0.20$^{a*}$ | 2.16 ± 0.27$^{*c}$ |
| UspA2 | CT-CRM$_{Y30WAH}$ | 1 µg | 3.84 ± 0.30* | 2.03 ± 0.34* |
|  |  | 0.1 µg | 2.05 ± 0.56 | <25 |
| UspA2 | CT-CRM$_{R25W}$ | 1 µg | 4.52 ± 0.46* | 2.52 ± 0.25* |
|  |  | 0.1 µg | 3.25 ± 0.39* | 1.28 ± 0.26 |
| UspA2 | CT-CRM$_{R25G}$ | 1 µg | 2.96 ± 0.33$^b$ | 1.53 ± 0.35$^d$ |
|  |  | 0.1 µg | 1.89 ± 0.27 | 1.20 ± 0.23 |
| UspA2 | Cholera Toxin | 1 µg | 4.61 ± 0.15* | 2.69 ± 0.31* |
|  |  | 0.1 µg | 4.44 ± 0.24* | 2.89 ± 0.23* |

The data reported in Table 17 was based upon the following experiment. Groups of five female BALB/c mice were immunized intranasally at weeks 0, 2, and 4 with 10 µL containing 5 µg nUspA2 adjuvanted with 1 µg CT (Sigma) or CT mutants. Endpoint antibody titers were determined from sera collected at week 6. Data are presented in Table 17 as the geometric mean (±1 SD) of the reciprocal dilution resulting in an OD$_{405}$ of 0.1. Statistical analysis by Tukey-Kramer indicated that results marked with an asterisk (*) were significantly higher than the nUspA2/PBS group.

TABLE 17

The serum anti-nUspA2 responses of BALB/c mice after intranasal immunization with nUspA2 adjuvanted with mutant CTs

| Group | Antigen (5 µg) | Adjuvant | Mean log 10 Antibody Titers (±1SD) IgG1 | IgG2a | IgG2b |
|---|---|---|---|---|---|
| AG673 | nUspA2 | PBS | <2.00 | <2.00 | <2.00 |
| AG674 | nUspA2 | CT-CRM$_{E29H}$ (1 µg) | 3.14 ± 0.23* | 3.44 ± 0.41* | 2.92 ± 0.20 |
| AG676 | nUspA2 | CT-CRM$_{T48TH}$ (1 µg) | 2.45 ± 0.31 | 2.85 ± 0.52* | 2.47 ± 0.33 |

TABLE 17-continued

The serum anti-nUspA2 responses of BALB/c mice after intranasal immunization with nUspA2 adjuvanted with mutant CTs

| | Antigen | | Mean log 10 Antibody Titers (±1SD) | | |
|---|---|---|---|---|---|
| Group | (5 μg) | Adjuvant | IgG1 | IgG2a | IgG2b |
| AG678 | nUspA2 | CT-CRM$_{G34GGP}$ (1 μg) | 3.06 ± 0.16* | 3.55 ± 0.09* | 3.00 ± 0.02 |
| AG680 | nUspA2 | CT-CRM$_{Y30WAH}$ (1 μg) | 2.61 ± 0.28* | 2.77 ± 0.23* | 2.37 ± 0.27 |
| AG682 | nUspA2 | CT-CRM$_{R25W}$ (1 μg) | 3.29 ± 0.40* | 3.43 ± 0.57* | 3.07 ± 0.30 |
| AG684 | nUspA2 | CT-CRM$_{R25G}$ (1 μg) | 2.11 ± 0.18 | 2.05 ± 0.09 | <2.00 |
| AG686 | nUspA2 | CT (1 μg) | 3.14 ± 0.28* | 3.39 ± 0.27* | 3.24 ± 0.29 |

For the data in Table 18, BALB/c mice (5/group) were immunized IN with a 10 μl volume at weeks 0, 2 and 4. Mucosal wash samples were collected at week 6. UspA2 ELISA titers were determined at an endpoint of 0.1 at $OD_{405}$.

TABLE 18

UspA2 ELISA - Mucosal Antibody Titers

| Antigen | | | Bronch washes | | Nasal washes | | Vaginal washes | |
|---|---|---|---|---|---|---|---|---|
| (5 μg) | Adjuvant | Dose | IgG | IgA | IgG | IgA | IgG | IgA |
| UspA2 | — | — | <10 | <10 | <10 | <10 | <10 | <10 |
| UspA2 | CT-CRM$_{E29H}$ | 1 μg | 21 | <10 | <10 | 17 | 54 | 500 |
| | | 0.1 μg | <10 | <10 | <10 | <10 | <10 | <10 |
| UspA2 | CT-CRM$_{T48TH}$ | 1 μg | <10 | <10 | <10 | <10 | <10 | 293 |
| | | 0.1 μg | <10 | <10 | <10 | <10 | <10 | <10 |
| UspA2 | CT-CRM$_{G34GGP}$ | 1 μg | 22 | <10 | <10 | 12 | 46 | 1,103 |
| | | 0.1 μg | <10 | <10 | <10 | 18 | <10 | 617 |
| UspA2 | CT-CRM$_{Y30WAH}$ | 1 μg | 11 | <10 | <10 | <10 | 12 | 105 |
| | | 0.1 μg | <10 | <10 | <10 | <10 | <10 | <10 |
| UspA2 | CT-CRM$_{R25W}$ | 1 μg | 24 | <10 | <10 | 24 | <10 | 323 |
| | | 0.1 μg | <10 | <10 | <10 | <10 | <10 | 13 |
| UspA2 | CT-CRM$_{R25G}$ | 1 μg | <10 | <10 | <10 | <10 | <10 | <10 |
| | | 0.1 μg | <10 | <10 | <10 | <10 | <10 | <10 |
| UspA2 | Cholera Toxin | 1 μg | 41 | 24 | <10 | 14 | 19 | 990 |
| | | 0.1 μg | 24 | 10 | <10 | 47 | 41 | 460 |

EXAMPLE 8

The Immune Responses of BALB/c Mice Immunized with the Purified Native Fusion (F) Protein of Respiratory Syncytial Virus (RSV)

The capacity of the mutant CT-CRMs of the present invention to augment the mucosal immune responses against respiratory syncytial virus (RSV) proteins was examined using the purified native fusion (F) protein.

Naïve BALB/c mice (8-10 weeks of age, 5/group) were immunized (IN, 10 μl) at weeks 0 and 3 with native purified fusion (F) protein purified from the 248/404 strain of RSV. The protein (3 μg/dose) was prepared in mixture with 1.0 or 0.1 μg of the indicated CT-CRM. Control mice were immunized with F protein admixed with CT-CRM$_{E29H}$ alone, with wild-type CT, or with PBS. Serum (geometric mean titer±1 standard deviation) and bronchoalveolar (BAW), nasal (NW) and vaginal (VW) wash fluids were collected two weeks after secondary immunization for the determination of end-point anti-F protein total and subclass IgG and IgA titers by ELISA. The mucosal wash samples were pooled for the determination of endpoint titers.

The results from two experiments are presented in Tables 19 and 20.

TABLE 19

The Humoral Immune Response to BALB/c Mice after Intranasal Immunization with F Protein and CT-CRMs

| | | Geometric Mean Serum Anti-F Protein Ig Titers (Log$_{10}$) | | | |
|---|---|---|---|---|---|
| Antigen | Adjuvant (μg) | IgG | IgG1 | IgG2a | IgA |
| F protein | NONE | 2.6 ± 1.5 | 2.3 ± 1.3 | 2.0 ± 0.8 | <1.7 |
| F protein | CT-CRM$_{T48TH}$(1) | 5.7 ± 0.1 | 5.4 ± 0.2 | 4.5 ± 0.3 | 4.0 ± 0.3 |

TABLE 19-continued

The Humoral Immune Response to BALB/c Mice after Intranasal Immunization with F Protein and CT-CRMs

| Antigen | Adjuvant (μg) | Geometric Mean Serum Anti-F Protein Ig Titers ($Log_{10}$) | | | |
|---|---|---|---|---|---|
| | | IgG | IgG1 | IgG2a | IgA |
| F protein | CT-CRM$_{T48TH}$(0.1) | 4.3 ± 1.0 | 4.4 ± 1.0 | 3.5 ± 0.5 | 2.7 ± 0.9 |
| F protein | CT-CRM$_{G34GCP}$(1) | 5.8 ± 0.3 | 5.3 ± 0.2 | 4.9 ± 0.4 | 4.2 ± 0.2 |
| F protein | CT-CRM$_{G34GCP}$(0.1) | 5.4 ± 0.2 | 5.0 ± 0.3 | 4.1 ± 0.3 | 4.1 ± 0.2 |
| F protein | CT-CRM$_{Y30WAH}$(1) | 5.9 ± 0.4 | 5.1 ± 0.2 | 4.5 ± 0.3 | 3.9 ± 0.3 |
| F protein | CT-CRM$_{Y30WAH}$(0.1) | 4.7 ± 0.5 | 4.9 ± 0.4 | 3.6 ± 0.5 | 3.1 ± 0.5 |
| F protein | CT-CRM$_{R25W}$(1) | 6.1 ± 0.3 | 5.7 ± 0.3 | 4.5 ± 0.2 | 4.2 ± 0.2 |
| F protein | CT-CRM$_{R25W}$(0.1) | 5.5 ± 0.4 | 5.3 ± 0.4 | 4.2 ± 0.3 | 4.0 ± 0.1 |
| F protein | CT-CRM$_{R25G}$(1) | 5.4 ± 0.4 | 4.9 ± 0.6 | 4.0 ± 0.4 | 3.9 ± 0.2 |
| F protein | CT-CRM$_{R25G}$(0.1) | 3.8 ± 0.9 | 3.7 ± 0.8 | 3.0 ± 0.4 | 2.6 ± 0.8 |
| F protein | CT-CRM$_{E29H}$(1) | 5.9 ± 0.4 | 5.4 ± 0.4 | 4.8 ± 0.3 | 4.3 ± 0.1 |
| F protein | CT-CRM$_{E29H}$(0.1) | 5.9 ± 0.4 | 5.3 ± 0.2 | 4.5 ± 0.3 | 4.4 ± 0.3 |
| F protein | CT(1) | 5.6 ± 1.2 | 5.2 ± 1.1 | 4.5 ± 1.1 | 4.3 ± 0.8 |
| F protein | CT(0.1) | 5.0 ± 0.3 | 5.2 ± 0.3 | 4.5 ± 0.3 | 4.2 ± 0.2 |

TABLE 20

The Humoral Immune Response to BALB/c Mice after Intranasal Immunization with F Protein and Genetically Detoxified Mutants of CT

| Antigen | Adjuvant (μg) | Anti-F Protein Antibody Titers | | | | | |
|---|---|---|---|---|---|---|---|
| | | BAW | | NW | | VW | |
| | | IgG | IgA | IgG | IgA | IgG | IgA |
| F protein | NONE | <25 | <25 | 64 | <25 | <25 | <25 |
| F protein | CT-CRM$_{T48TH}$(1) | 227 | 33 | 146 | 2,560 | 112 | 2,065 |
| F protein | CT-CRM$_{T48TH}$(0.1) | 59 | 27 | <25 | 384 | <25 | 344 |
| F protein | CT-CRM$_{G34GCP}$(1) | 964 | 458 | 60 | 708 | 125 | 562 |
| F protein | CT-CRM$_{G34GCP}$(0.1) | 181 | <25 | 117 | 352 | 57 | 755 |
| F protein | CT-CRM$_{Y30WAH}$(1) | 312 | <25 | <25 | 177 | 52 | 1,332 |
| F protein | CT-CRM$_{Y30WAH}$0.1) | 111 | 24 | 63 | 210 | <25 | 139 |
| F protein | CT-CRM$_{R25W}$(1) | 200 | 33 | 34 | 378 | 35 | 665 |
| F protein | CT-CRM$_{R25W}$(0.1) | 137 | 32 | 61 | 557 | 55 | 633 |
| F protein | CT-CRM$_{R25G}$(1) | 230 | 42 | 22 | 283 | <25 | 307 |
| F protein | CT-CRM$_{R25G}$(0.1) | 44 | <25 | <25 | 39 | <25 | 125 |
| F protein | CT-CRM$_{E29H}$(1) | 277 | 59 | 846 | 932 | 18 | 832 |
| F protein | CT-CRM$_{E29H}$(0.1) | 142 | 60 | 245 | 239 | <25 | 496 |
| F protein | CT(1) | 398 | 114 | 68 | 504 | <25 | 981 |
| F protein | CT(0.1) | 158 | <25 | <25 | 360 | 189 | 903 |

When the CT-CRM mutants of this invention were used as mucosal adjuvants at the 1.0 μg dose, results similar to the use of mutant CT-CRM$_{E29H}$ or wild-type CT were obtained (Table 19). Noteworthy differences from the anti-F protein IgG or IgA titers elicited following immunization with F protein admixed with CT-CRM$_{E29H}$ or wild-type CT were not observed. However, at the 0.1 μg dose, CT-CRM$_{T48TH}$, CT-CRM$_{Y30WAH}$ and CT-CRM$_{R25G}$ appeared less able to augment serum anti-F protein IgA titers. The titers in the mucosal wash fluids of rice immunized with F protein formulated with the mutants of this invention appeared comparable to those induced by F protein admixed with CT-CRM$_{E29H}$ or wild-type CT (Table 20).

Thus, all CT-CRM mutants of this invention had adjuvant activity for F protein.

All publications and references cited in this specification are incorporated herein by reference. While the invention has been described with reference to a particularly preferred embodiment, it will be appreciated that modifications can be made without departing from the spirit of the invention. Such modifications are intended to fall within the scope of the appended claims.

The invention claimed is:

1. An immunogenic, mutant cholera holotoxin (CT-CRM) comprising an amino acid sequence of subunit A of the wild-type cholera holotoxin (CT), wherein the amino acid arginine in the amino acid position 25 in the A subunit is substituted with a typtophan or a glycine, wherein the mutant CT-CRM has reduced toxicity compared to wild-type CT.

2. The CT-CRM according to claim 1, wherein the amino acid arginine in the amino acid position 25 in the A subunit is substituted with a glycine.

3. The CT-CRM according to claim 1, wherein the amino acid arginine in the amino acid position 25 in the A subunit is substituted with a tryptophan.

4. An immunogenic composition comprising an immunogenic, mutant cholera holotoxin (CT-CRM) comprising an amino acid sequence of subunit A of the wild-type cholera toxin (CT), wherein the amino acid arginine in the amino acid position 25 in the A subunit is substituted with a tryptophan or a glycine, wherein the mutant holotoxin enhances the immune response in a vertebrate host to an antigen.

5. The immunogenic composition according to claim 4, wherein the amino acid arginine in the amino acid position 25 in the A subunit is substituted with a glycine.

6. The composition according to claim 4, further comprising a diluent, excipient or carrier.

7. The composition according to claim 4, further comprising a second adjuvant in addition to the mutant cholera holotoxin.

8. The immunogenic composition according to claim 4, wherein the amino acid arginine in the amino acid position 25 in the A subunit is substituted with a tryptophan.

9. The composition according to claim 4, further comprising an antigen selected from the group consisting of a pathogenic bacterium, a pathogenic virus, a pathogenic fungus and a pathogenic parasite, a cancer cell, a tumor cell, an allergen and a self-molecule, and a protein, polypeptide, peptide or fragment derived from said antigen.

10. The composition according to claim 9, wherein the selected fungal antigen is derived from a fungus selected from the group of pathogenic fungi consisting of *Aspergillis, Blastomyces, Candida, Coccidiodes, Cryptococcus* and *Histoplasma.*

11. The composition according to claim 9, wherein the parasite antigen is from a parasite selected from the group of pathogenic parasites consisting of *Leishmania major, Ascaris, Trichuris, Giardia, Schistoma, Cryptosporidium, Trichomonas, Toxoplasma gondii* and *Pneumocystis carinii.*

12. The composition according to claim 9, wherein said cancer or tumor cell antigen is selected from the group consisting of prostate specific antigen, carcino-embryonic antigen, MUC-1, Her2, CA-125, MAGE-3, a hormone, and a hormone analogs.

13. The composition according to claim 9, wherein said antigen is a polypeptide, peptide or fragment derived from amyloid precursor protein, or an allergen.

14. The composition according to claim 9, wherein the bacterial antigen is selected from a bacterial species consisting of typable and non-typable *Haemophilus influenzae, Haemophilus somnus, Moraxella catarrhalis, Streptococcus pneumoniae, Streptococcus pyogenes, Streptococcus agalactiae, Streptococcus faecalis, Helicobacter pylori, Neisseria meningitidis, Neisseria gonorrhoeae, Chlamydia trachomatis, Chlamydia pneumoniae, Chlamydia psittaci, Bordetella pertussis, Alloiococcus otiditis, Salmonella typhi, Salmonella typhimurium, Salmonella choleraesuis, Escherichia coli, Shigella, Vibrio cholerae, Cotynebacterium diptheriae, Mycobacterium tuberculosis, Mycobacterium avium-Mycobacterium intracellular complex, Proteus mirabilis, Proteus vulgaris, Staphylococcus aureus, Staphylococcus epidermis, Clostridium tetani, Leptospira interrogans,*

*Borrelia burdorferi, Pasteurella haemolytica, Pasteurella multocida, Actinobacillus pleauropneumoniae* and *Mycoplasma galliseptium*.

15. The composition according to claim 14, wherein the *Haemophilus influenza* antigen is selected from the group consisting of the *Haemophilus influenzae* P4 outer membrane protein, the *Haemophilus influenzae* P6 outer membrane protein and *Haemophilus influenzae* adherence and penetration protein (Hap$_s$).

16. The composition according to claim 15, wherein the *Helicobacter Pylon* antigen is the *Helicobacter pylori* urease protein.

17. The composition according to claim 15, wherein the *Neisseria meningitidis* antigen is selected from the group consisting of the *Neisseria meningitidis* Group B recombinant class 1 pilin (rpilin) and the *Neisseria meningitidis* Group B class 1 outer membrane protein (porA).

18. The composition according to claim 9, wherein the viral antigen is selected from the viral species consisting of Respiratory syncytial virus, Parainfluenza virus types 1, 2, 3, Human metapneumovirus, Influenza virus, Herpes simplex virus, Human cytomegalovirus, Human immunodeficiency virus, Hepatitis A virus, Hepatitis B virus, Hepatitis C virus, Human papillomavirus, poliovirus, rotavirus, caliciviruses, measles virus, mumps virus, Rubella virus, adenovirus, rabies virus, canine distemper virus, rinderpest virus, avian pneumovirus, Hendra virus, Nipah virus, coronavirus, parvovirus, infectious rhinotracheitis viruses, feline leukemia virus, feline infectious peritonitis virus, avian infectious bursal disease virus, Newcastle disease virus, Marek's disease virus, porcine respiratory and reproductive syndrome virus, equine arteritis virus and the encephalitis viruses.

19. The composition according to claim 18, wherein the respiratory syncytial virus is the respiratory syncytial virus fusion protein.

20. The composition according to claim 18, wherein the herpes simplex virus (HSV) antigen is the herpes simplex virus (HSV) type 2 glycoprotein D (gD2).

21. The composition according to claim 9, wherein the amyloid precursor protein is the Aβ peptide, which is a 42 amino acid fragment of amyloid precursor protein, or a fragment of the Aβ peptide.

* * * * *

UNITED STATES PATENT AND TRADEMARK OFFICE
CERTIFICATE OF CORRECTION

PATENT NO. : 7,332,174 B2
APPLICATION NO. : 10/478308
DATED : February 19, 2008
INVENTOR(S) : Green et al.

Page 1 of 1

It is certified that error appears in the above-identified patent and that said Letters Patent is hereby corrected as shown below:

1. Col. 53, Line 36, replace "typtophan" with -- "tryptophan" --.

2. Col. 54, Line 63, replace "cotynebacterium" with -- "corynebacterium --.

Signed and Sealed this

Twenty-fourth Day of June, 2008

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,332,174 B2 | Page 1 of 1 |
| APPLICATION NO. | : 10/478308 | |
| DATED | : February 19, 2008 | |
| INVENTOR(S) | : Bruce A. Green et al. | |

It is certified that error appears in the above-identified patent and that said Letters Patent is hereby corrected as shown below:

On the Title page,

[*] Notice: Subject to any disclaimer, the term of this patent is extended or adjusted under 35 U.S.C. 154(b) by 507 days.

Delete the phrase "by 507 days" and insert -- by 1069 days --

Signed and Sealed this

Twenty-fourth Day of August, 2010

David J. Kappos
*Director of the United States Patent and Trademark Office*

SEQUENCE LISTING

<160> NUMBER OF SEQ ID NOS: 6

<210> SEQ ID NO 1
<211> LENGTH: 382
<212> TYPE: PRT
<213> ORGANISM: Vibrio cholerae

<400> SEQUENCE: 1

```
Met Val Lys Ile Ile Phe Val Phe Phe Ile Phe Leu Ser Ser Phe Ser
1               5                  10                  15

Tyr Ala Asn Asp Asp Lys Leu Tyr Arg Ala Asp Ser Arg Pro Pro Asp
            20                  25                  30

Glu Ile Lys Gln Ser Gly Gly Leu Met Pro Arg Gly Gln Ser Glu Tyr
        35                  40                  45

Phe Asp Arg Gly Thr Gln Met Asn Ile Asn Leu Tyr Asp His Ala Arg
    50                  55                  60

Gly Thr Gln Thr Gly Phe Val Arg His Asp Asp Gly Tyr Val Ser Thr
65                  70                  75                  80

Ser Ile Ser Leu Arg Ser Ala His Leu Val Gly Gln Thr Ile Leu Ser
                85                  90                  95

Gly His Ser Thr Tyr Tyr Ile Tyr Val Ile Ala Thr Ala Pro Asn Met
            100                 105                 110

Phe Asn Val Asn Asp Val Leu Gly Ala Tyr Ser Pro His Pro Asp Glu
        115                 120                 125

Gln Glu Val Ser Ala Leu Gly Gly Ile Pro Tyr Ser Gln Ile Tyr Gly
    130                 135                 140

Trp Tyr Arg Val His Phe Gly Val Leu Asp Glu Gln Leu His Arg Asn
145                 150                 155                 160

Arg Gly Tyr Arg Asp Arg Tyr Tyr Ser Asn Leu Asp Ile Ala Pro Ala
                165                 170                 175

Ala Asp Gly Tyr Gly Leu Ala Gly Phe Pro Pro Glu His Arg Ala Trp
            180                 185                 190

Arg Glu Glu Pro Trp Ile His His Ala Pro Pro Gly Cys Gly Asn Ala
        195                 200                 205

Pro Arg Ser Ser Met Ser Asn Thr Cys Asp Glu Lys Thr Gln Ser Leu
    210                 215                 220

Gly Val Lys Phe Leu Asp Glu Tyr Gln Ser Lys Val Lys Arg Gln Ile
225                 230                 235                 240

Phe Ser Gly Tyr Gln Ser Asp Ile Asp Thr His Asn Arg Ile Lys Asp
                245                 250                 255

Glu Leu Met Ile Lys Leu Lys Phe Gly Val Phe Phe Thr Val Leu Leu
            260                 265                 270

Ser Ser Ala Tyr Ala His Gly Thr Pro Gln Asn Ile Thr Asp Leu Cys
        275                 280                 285

Ala Glu Ser His Asn Thr Gln Ile Tyr Thr Leu Asn Asp Lys Ile Phe
    290                 295                 300

Ser Tyr Thr Glu Ser Leu Ala Gly Lys Arg Glu Met Ala Ile Ile Thr
305                 310                 315                 320

Phe Lys Asn Gly Ala Ile Phe Gln Val Glu Val Pro Ser Ser Gln His
                325                 330                 335

Ile Asp Ser Gln Lys Lys Ala Ile Glu Arg Met Lys Asp Thr Leu Arg
            340                 345                 350

Ile Ala Tyr Leu Thr Glu Ala Lys Val Glu Lys Leu Cys Val Trp Asn
        355                 360                 365

Asn Lys Thr Pro His Ala Ile Ala Ala Ile Ser Met Ala Asn
    370                 375                 380
```

<210> SEQ ID NO 2
<211> LENGTH: 240
<212> TYPE: PRT
<213> ORGANISM: Vibrio cholerae

```
<400> SEQUENCE: 2

Asn Asp Asp Lys Leu Tyr Arg Ala Asp Ser Arg Pro Pro Asp Glu Ile
1               5                   10                  15

Lys Gln Ser Gly Gly Leu Met Pro Arg Gly Gln Ser Glu Tyr Phe Asp
            20                  25                  30

Arg Gly Thr Gln Met Asn Ile Asn Leu Tyr Asp His Ala Arg Gly Thr
        35                  40                  45

Gln Thr Gly Phe Val Arg His Asp Asp Gly Tyr Val Ser Thr Ser Ile
    50                  55                  60

Ser Leu Arg Ser Ala His Leu Val Gly Gln Thr Ile Leu Ser Gly His
65                  70                  75                  80

Ser Thr Tyr Tyr Ile Tyr Val Ile Ala Thr Ala Pro Asn Met Phe Asn
                85                  90                  95

Val Asn Asp Val Leu Gly Ala Tyr Ser Pro His Pro Asp Glu Gln Glu
            100                 105                 110

Val Ser Ala Leu Gly Gly Ile Pro Tyr Ser Gln Ile Tyr Gly Trp Tyr
        115                 120                 125

Arg Val His Phe Gly Val Leu Asp Glu Gln Leu His Arg Asn Arg Gly
    130                 135                 140

Tyr Arg Asp Arg Tyr Tyr Ser Asn Leu Asp Ile Ala Pro Ala Ala Asp
145                 150                 155                 160

Gly Tyr Gly Leu Ala Gly Phe Pro Pro Glu His Arg Ala Trp Arg Glu
                165                 170                 175

Glu Pro Trp Ile His His Ala Pro Pro Gly Cys Gly Asn Ala Pro Arg
            180                 185                 190

Ser Ser Met Ser Asn Thr Cys Asp Glu Lys Thr Gln Ser Leu Gly Val
        195                 200                 205

Lys Phe Leu Asp Glu Tyr Gln Ser Lys Val Lys Arg Gln Ile Phe Ser
    210                 215                 220

Gly Tyr Gln Ser Asp Ile Asp Thr His Asn Arg Ile Lys Asp Glu Leu
225                 230                 235                 240

<210> SEQ ID NO 3
<211> LENGTH: 42
<212> TYPE: PRT
<213> ORGANISM: artificial sequence
<220> FEATURE:
<223> OTHER INFORMATION: beta-amyloid peptide

<400> SEQUENCE: 3

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 4
<211> LENGTH: 28
<212> TYPE: PRT
<213> ORGANISM: artificial sequence
<220> FEATURE:
<223> OTHER INFORMATION: alpha-beta-amyloid peptide
```

-continued

```
<400> SEQUENCE: 4

Asp Ala Glu Phe Arg His Asp Ser Gly Tyr Glu Val His His Gln Lys
1               5                   10                  15

Leu Val Phe Phe Ala Glu Asp Val Gly Ser Asn Lys
            20                  25

<210> SEQ ID NO 5
<211> LENGTH: 32
<212> TYPE: DNA
<213> ORGANISM: Artificial sequence
<220> FEATURE:
<223> OTHER INFORMATION: primer sequence

<400> SEQUENCE: 5 tttttgggc tagcatggag gaaaagatga gc                                      32

<210> SEQ ID NO 6
<211> LENGTH: 26
<212> TYPE: DNA
<213> ORGANISM: Artificial sequence
<220> FEATURE:
<223> OTHER INFORMATION: primer sequence

<400> SEQUENCE: 6
cgaggtcgaa gcttgcatgt ttgggc                                            26
```